United States Patent
Davis et al.

(10) Patent No.: US 9,908,829 B2
(45) Date of Patent: Mar. 6, 2018

(54) PROCESS FOR MAKING PHENOL AND/OR CYCLOHEXANONE

(71) Applicant: ExxonMobil Chemical Patents Inc., Baytown, TX (US)

(72) Inventors: Jason D. Davis, Beaumont, TX (US); Ashley J. Poucher, Houston, TX (US); Jörg F. W. Weber, Houston, TX (US); Jonathan J. Watts, Houston, TX (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/038,975

(22) PCT Filed: Nov. 14, 2014

(86) PCT No.: PCT/US2014/065789
§ 371 (c)(1),
(2) Date: May 24, 2016

(87) PCT Pub. No.: WO2015/094530
PCT Pub. Date: Jun. 25, 2015

(65) Prior Publication Data
US 2016/0376210 A1   Dec. 29, 2016

Related U.S. Application Data

(60) Provisional application No. 61/919,345, filed on Dec. 20, 2013.

(30) Foreign Application Priority Data

Mar. 5, 2014   (EP) ..................................... 14157824

(51) Int. Cl.
| C07C 45/53 | (2006.01) |
| C07C 37/08 | (2006.01) |
| C07C 407/00 | (2006.01) |
| C07C 2/74 | (2006.01) |
| C07C 37/80 | (2006.01) |

(52) U.S. Cl.
CPC ................ *C07C 37/08* (2013.01); *C07C 2/74* (2013.01); *C07C 37/80* (2013.01); *C07C 45/53* (2013.01); *C07C 407/00* (2013.01); *C07C 2601/14* (2017.05); *C07C 2601/16* (2017.05)

(58) Field of Classification Search
CPC ....... C07C 45/53; C07C 37/08; C07C 407/00; C07C 2/74
See application file for complete search history.

(56) References Cited

U.S. PATENT DOCUMENTS

| 3,322,651 | A | 5/1967 | Nielsen |
| 3,793,383 | A | 2/1974 | Johnson et al. |
| 4,122,125 | A | 10/1978 | Murtha et al. |
| 4,206,082 | A | 6/1980 | Johnson et al. |
| 4,217,248 | A | 8/1980 | Murtha et al. |
| 4,439,409 | A | 3/1984 | Puppe et al. |
| 4,826,667 | A | 5/1989 | Zones et al. |
| 4,954,325 | A | 9/1990 | Rubin et al. |
| 5,064,507 | A | 11/1991 | O'Donnell et al. |
| 5,236,575 | A | 8/1993 | Bennett et al. |
| 5,250,277 | A | 10/1993 | Kresge et al. |
| 5,362,697 | A | 11/1994 | Fung et al. |
| 6,037,513 | A | 3/2000 | Chang et al. |
| 6,049,018 | A | 4/2000 | Calabro et al. |
| 6,077,498 | A | 6/2000 | Diaz Cabanas et al. |
| 6,720,462 | B2 | 4/2004 | Kuhnle et al. |
| 6,730,625 | B1 | 5/2004 | Chang et al. |
| 6,756,030 | B1 | 6/2004 | Rohde et al. |
| 6,797,193 | B2 | 9/2004 | Brown et al. |
| 7,199,271 | B2 | 4/2007 | Fodor |
| 7,579,511 | B1 | 8/2009 | Dakka et al. |
| 7,847,128 | B2 | 12/2010 | Chen et al. |
| 8,178,728 | B2 | 5/2012 | Cheng et al. |
| 8,519,194 | B2 | 8/2013 | Chen et al. |
| 8,884,067 | B2 | 11/2014 | Kuechler et al. |
| 9,108,893 | B2 | 8/2015 | Nair et al. |
| 9,174,908 | B2 * | 11/2015 | Davis ..................... C07C 45/82 568/347 |
| 2005/0137429 | A1 | 6/2005 | Tatake et al. |
| 2013/0172514 | A1 | 7/2013 | Xu et al. |
| 2013/0217921 | A1 | 8/2013 | Kuechler et al. |
| 2013/0277605 | A1 | 10/2013 | Kuechler et al. |

FOREIGN PATENT DOCUMENTS

| CN | 101796000 | 8/2010 |
| EP | 0 293 032 | 11/1988 |
| WO | 97/17290 | 5/1997 |
| WO | 01/47840 | 7/2001 |
| WO | 2009/128984 | 10/2009 |
| WO | 2009/131769 | 10/2009 |
| WO | 2010/138248 | 12/2010 |
| WO | 2012/036818 | 3/2012 |
| WO | 2012/036821 | 3/2012 |
| WO | 2012/036830 | 3/2012 |
| WO | 2012/082229 | 6/2012 |
| WO | 2012/082232 | 6/2012 |
| WO | 2013/130144 | 9/2013 |

* cited by examiner

*Primary Examiner* — Sikarl Witherspoon

(57) ABSTRACT

Disclosed is (i) a process of making phenol and/or cyclohexanone from cyclohexylbenzene including a step of removing methylcyclopentylbenzene from (a) the cyclohexylbenzene feed supplied to the oxidation step and/or (b) the crude phenol product (ii) a phenol composition and (iii) a cyclohexylbenzene composition that can be made using the process.

10 Claims, 1 Drawing Sheet

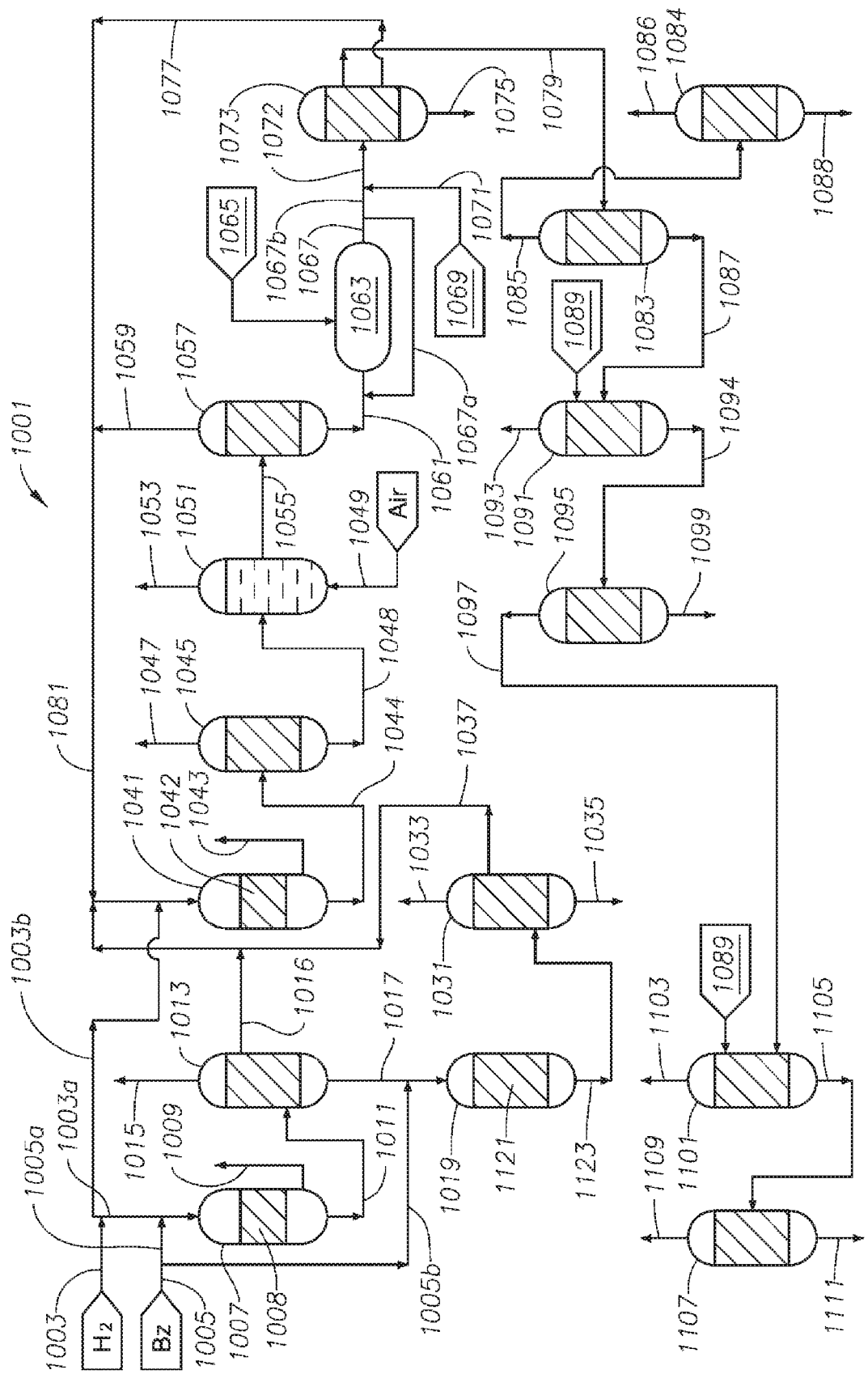

PROCESS FOR MAKING PHENOL AND/OR CYCLOHEXANONE

CROSS-REFERENCE TO RELATED APPLICATIONS

This application is a National Stage Application of International Application No. PCT/US2014/065789 filed Nov. 14, 2014, which claims the benefit of Ser. No. 61/919,345, filed Dec. 20, 2013, and EP 14157824.5 filed Mar. 5, 2014, the disclosures of which are incorporated herein by reference in their entireties.

FIELD

The present disclosure relates to a process for making phenol and/or cyclohexanone, and phenol and cyclohexylbenzene that can be made by such process.

BACKGROUND

Phenol and cyclohexanone are important compounds in the chemical industry and are useful in, for example, production of phenolic resins, bisphenol A, ε-caprolactam, adipic acid, and plasticizers.

Currently, a common route for the production of phenol is the Hock process. This is a three-step process in which the first step involves alkylation of benzene with propylene to produce cumene, followed by oxidation of cumene to the corresponding hydroperoxide, and then cleavage of the hydroperoxide to produce equimolar amounts of phenol and acetone. However, the world demand for phenol is growing more rapidly than that for acetone.

Thus, a process that uses higher alkenes instead of propylene as feed and coproduces higher ketones, such as cyclohexanone, rather than acetone may be an attractive alternative route to the production of phenols. There is also a growing demand for cyclohexanone.

It is known from, e.g., U.S. Pat. No. 6,037,513, that cyclohexylbenzene can be produced by contacting benzene with hydrogen in the presence of a bifunctional catalyst comprising a molecular sieve of the MCM-22 type and at least one hydrogenation metal selected from palladium, ruthenium, nickel, cobalt, and mixtures thereof. This reference also discloses that the resultant cyclohexylbenzene can be oxidized to the corresponding hydroperoxide which can then be decomposed to produce phenol and cyclohexanone. This cyclohexylbenzene-based process for co-producing phenol and cyclohexanone can be highly efficient in making these two important industrial materials.

SUMMARY

Methylcyclopentylbenzene is produced as a by-product in hydroalkylation of benzene. It has been found in a surprising manner that methylcyclopentylbenzene thus produced can contaminate the end phenol product. Furthermore, similar to cyclohexylbenzene, part of methylcyclopentylbenzene will be oxidized to methyl cyclopentylbenzene hydroperoxide, and eventually converted into phenol and methylcyclopentanone in the cleavage step. The methylcyclopentanone thus produced can contaminate the cyclohexanone product because they have close boiling points.

As such, there is a need for: (i) processes for making high-purity phenol and cyclohexanone products with low level of contamination by methylcyclopentylbenzene and methylcyclopentanone; (ii) a phenol product with low level of contamination by methylcyclopentylbenzene, and (iii) a cyclohexylbenzene intermediate with low level of contamination by methylcyclopentylbenzene.

The present invention satisfies this and other needs.

Accordingly, in one aspect, the present disclosure relates to a process for making phenol and/or cyclohexanone, the process comprising:
(I) providing a first mixture comprising cyclohexylbenzene and methylcyclopentylbenzene;
(II) removing at least a portion of the methylcyclopentylbenzene from the first mixture to obtain a second mixture comprising cyclohexylbenzene.
(III) oxidizing at least a portion of the cyclohexylbenzene in the second mixture in an oxidation reactor under oxidation conditions to obtain a third mixture comprising cyclohexylbenzene hydroperoxide and cyclohexylbenzene; and
(IV) reacting at least a portion of the third mixture in a cleavage reactor under cleavage reaction conditions to obtain a cleavage product mixture comprising cyclohexylbenzene, phenol and cyclohexanone.

In a second aspect, the present disclosure relates to another process for making phenol and/or cyclohexanone, the process comprising:
(A) contacting benzene with hydrogen in the presence of a hydroalkylation catalyst under hydroalkylation conditions to obtain a hydroalkylation product mixture comprising cyclohexylbenzene;
(B) oxidizing at least a portion of the cyclohexylbenzene in an oxidation reactor under oxidation conditions to obtain an oxidation product mixture comprising cyclohexylbenzene hydroperoxide and cyclohexylbenzene;
(C) cleaving at least a portion of the cyclohexylbenzene hydroperoxide in a cleavage reactor under cleavage conditions to obtain a cleavage product mixture comprising cyclohexylbenzene, phenol, and cyclohexanone;
(D) separating the cleavage product mixture to obtain a cyclohexylbenzene fraction, a phenol fraction comprising methylcyclopentylbenzene, and a cyclohexanone fraction; and
(E) removing at least a portion of the methylcyclopentylbenzene from the phenol fraction.

BRIEF DESCRIPTION OF THE DRAWINGS

FIG. 1 is a schematic diagram showing a process/system of the present invention for making phenol and cyclohexanone starting from benzene hydroalkylation including a step of removing methylcyclopentylbenzene from cyclohexylbenzene before oxidation.

DETAILED DESCRIPTION

In the present disclosure, a process is described as comprising at least one "step." It should be understood that each step is an action or operation that may be conducted once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be conducted simultaneously with respect to an intermediate material resulting from treating the raw materials fed into the process at an earlier time in the first step. Preferably, steps are performed in the order listed.

Unless otherwise indicated, all numbers indicating quantities in the present disclosure are to be understood as being modified by the term "about" in all instances should also be understood that the precise numerical values used in the specification and claims constitute specific examples. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, processes using "a hydrogenation metal" include those where one, two or more different types of the hydrogenation metals are used, unless specified to the contrary or the context clearly indicates that only one type of the hydrogenation metal is used.

As used herein, "wt %" means percentage by weight, "vol %" means percentage by volume, "mol %" means percentage by mole, "ppm" means parts per million, "ppb" means parts per billion, "ppm wt" and "wppm" are used interchangeably to mean parts per million on a weight basis, and "ppb wt" and "wppb" are used interchangeably to mean parts per billion on a weight basis. All "ppm" and "ppb" as used herein are ppm and ppb by weight unless specified otherwise. All concentrations herein are expressed on the basis of the total amount of the composition in question unless specified or indicated otherwise. All ranges expressed herein should include both end points as two specific examples unless specified or indicated to the contrary.

As used herein, the generic term "dicyclohexylbenzene" (DiCHB) includes, in the aggregate, 1,2-dicyclohexylbenzene, 1,3-dicylohexylbenzene, and 1,4-dicyclohexylbenzene, unless clearly specified to mean only one or two thereof. The term cyclohexylbenzene, when used in singular form, means mono substituted cyclohexylbenzene. As used herein, the generic term "tricyclohexylbenzene" (TriCHB) includes, in the aggregate, 1,2,3-tricyclohexylbenzene, 1,2,4-tricylohexylbenzene, and 1,3,5-tricyclohexylbenzene, unless clearly specified to mean only one or two thereof.

As used herein, the generic term "methylcyclopentylbenzene" (MCPB) includes, in the aggregate, 1-methyl-1-phenylcyclopentane (MCPB1), cis-1-methyl-2-phenylcyclopentane (MCPB2cis), trans-1-methyl-2-phenylcyclopentane (MCPB2trans), cis-1-methyl-3-phenylcyclopentane (MCPB3cis), and trans-1-methyl-3-phenylcyclopentane (MCPB3trans). The generic term MCPB2 (or MCPB2s) includes, in the aggregate, MCPB2cis and MCPB2trans. The generic term MCPB3 (or MCPB3s) includes, in the aggregate, MCPB3cis and MCPB3trans.

The term "MCM-22 type material" (or "material of the MCM-22 type" or "molecular sieve of the MCM-22 type" or "MCM-22 type zeolite"), as used herein, includes one or more of:

molecular sieves made from a common first degree crystalline building block unit cell, which unit cell has the MWW framework topology. A unit cell is a spatial arrangement of atoms which if tiled in three-dimensional space describes the crystal structure. Such crystal structures are discussed in the "Atlas of Zeolite Framework Types," Fifth Edition, 2001, the entire content of which is incorporated as reference;

molecular sieves made from a common second degree building block, being a 2-dimensional tiling of such MWW framework topology unit cells, forming a monolayer of one unit cell thickness, desirably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 type include those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques such as using the K-alpha doublet of copper as incident radiation and a diffractometer equipped with a scintillation counter and associated computer as the collection system.

Non-limiting examples of materials of the MCM-22 type include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Other molecular sieves, such as UZM-8 (described in U.S. Pat. No. 6,756,030), may be used alone or together with the MCM-22 type molecular sieves as well for the purpose of the present disclosure. Desirably, the molecular sieve is selected from (a) MCM-49; (b) MCM-56; and (c) isotypes of MCM-49 and MCM-56, such as ITO-2.

The process of co-producing phenol and cyclohexanone from benzene hydroalkylation involves three reaction steps: (i) hydroalkylation of benzene to make cyclohexylbenzene; (ii) oxidation of cyclohexylbenzene to make cyclohexylbenzene hydroperoxide; and (iii) cleavage of cyclohexylbenzene hydroperoxide to make phenol and cyclohexanone. The cleavage mixture is subsequently separated and purified to make the targeted products phenol and cyclohexanone. Cyclohexanone is typically used for making caprolactam, which, in turn, is used primarily for making nylon-6, an important polymer material.

Methylcyclopentylbenzene is produced at a non-negligible amount in the hydroalkylation of benzene in the presence of a hydroalkylation catalyst, or the alkylation of benzene by cyclohexene in the presence of an alkylation catalyst, to make cyclohexylbenzene. In the subsequent oxidation step, methylcyclopentylbenzene, if present in the cyclohexylbenzene feed, can be oxidized to form corresponding methylcyclopentylbenzene hydroperoxide. In the cleavage step, the methylcyclopentylbenzene hydroperoxide, if present in the cyclohexylbenzene hydroperoxide feed, cleaves to form methylcyclopentanone and phenol.

Methylcyclopentanone has a boiling point very close to that of cyclohexanone, and thus is difficult to remove from the cyclohexanone product. The methylcyclopentanone contaminants in the cyclohexanone product, even if present at low concentrations, can negatively impact the quality of caprolactam intermediate product and the end product nylon-6 significantly. Therefore, there is a need to remove methylcyclopentanone from the cyclohexanone product, or a desire to minimize the production of methylcyclopentanone in the cleavage step.

Furthermore, in the oxidation step, the conversion of cyclohexylbenzene to cyclohexylbenzene hydroperoxide is typically lower than 50 wt %. As such, a significant amount of cyclohexylbenzene is carried over to the cleavage step, even if a step of removing part of the unreacted cyclohexylbenzene from the oxidation reaction effluent is carried out before cleavage, which will end up in the cleavage product mixture. Given the similar physical and chemical properties of methylcyclopentylbenzene and cyclohexylbenzene, a significant proportion of MCPB, if present in the teed to the oxidation step, will be carried over to the cleavage step, and end up in the cleavage product mixture as well.

We found that methylcyclopentylbenzene as produced in the hydroalkylation step has the following primary isomers shown below as MCPB1, MCPB2cis, MCPB2trans, MCPB3cis, and MCPB3trans. We found that: (i) cyclohexylbenzene has a higher normal boiling point than any of the methylcyclopentylbenzene isomers listed below; (ii) among all these methylcyclopentylbenzene isomers, MCPB2trans has the lowest normal boiling temperature, followed by MCPB1, then the MCPB3s, and then MCPB2cis; and (iii) in a surprising manner, MCPB2cis has a normal boiling temperature about 8-10° C. higher than MCPB2trans.

TABLE

| Code Name | | Structural Formula | Chemical Name |
|---|---|---|---|
| MCPB | MCPB1 | CH₃, Ph on cyclopentane | 1-methyl-1-phenyl-cyclopentane |
| | MCPB2cis | Ph, CH₃ (cis) on cyclopentane | cis-1-methyl-2-phenyl-cyclopentane |
| | MCPB2trans | Ph, CH₃ (trans) on cyclopentane | trans-1-methyl-2-phenyl-cyclopentane |
| MCPB3 | MCPB3cis | Ph, CH₃ (cis) on cyclopentane | cis-1-methyl-3-phenyl-cyclopentane |
| | MCPB3trans | Ph, CH₃ (trans) on cyclopentane | trans-1-methyl-3-phenyl-cyclopentane |

While essentially all cyclohexylbenzene contained in the cleavage product mixture can be removed and separated from the cyclohexanone and phenol products by conventional distillation, the removal of methylcyclopentylbenzene proved to be tricky and more difficult. It has been found that, in a typical benzene hydroalkylation process, (i) MCPB2trans and MCPB2cis (collectively (MCPB2s)) can be produced at a much higher concentration than MCPB3cis and MCPB3trans (collectively (MCPB3s)); (ii) the MCPB2s can be produced at a much higher concentration than MCPB1; and (iii) MCPB2trans can be produced at a much higher concentration than MCPB2cis. It has been found that MCPB2cis oxidation is much faster than MCPB2trans. As such, after cleavage, among all the MCPB isomers listed above, MCPB2trans tends to have the highest concentration if no attempt is made to remove part of methylcyclopentylbenzene from the cyclohexylbenzene feed to the oxidation step. The MCPB isomers, especially MCPB2trans, if present in the cleavage product mixture, are very difficult to separate from phenol by routine distillation because they have close normal boiling is temperatures. Furthermore, it is believed that MCPB2trans forms a non-ideal mixture (e.g. an azeotrope) with phenol under normal conditions, making complete separation thereof using normal distillation virtually impossible. In general, methylcyclopentylbenzene, if present in phenol at high concentration, can be highly undesirable as it can interfere with the downstream use of the phenol product, such as in the production of high-purity bisphenol-A and high-performance polycarbonate polymer materials.

We have found that by removing at least a portion of the methylcyclopentylbenzene from cyclohexylbenzene before oxidation, one can effectively achieve two goals at the some time: (i) reducing the amount of methylcyclopentanone by-products produced in the cleavage step, thereby reducing or eliminating the need of removing methylcyclopentanone from the cyclohexanone product; and (ii) reducing the amount of methylcyclopentylbenzene contaminants in the cleavage product mixture, thereby reducing or eliminating the need of removing methylcyclopentylbenzene contaminants from the phenol product. The methylcyclopentylbenzene removing step can be carried out with respect to one of more of the following: (a) the cyclohexylbenzene stream produced from the hydroalkylation and transalkylation steps; (b) the cyclohexylbenzene stream produced from the cyclohexylbenzene hydroperoxide concentrator following the oxidation reactor; and (c) the cyclohexylbenzene stream produced from the separation step after cleavage. We have also found that, if necessary, methylcyclopentylbenzene contaminants contained in a phenol composition can be effectively reduced to a very low level by using extractive distillation with the help of an extractive solvent. As a result, the present invention provides high-quality phenol and cyclohexanone products with low level of contaminants.

Supply of Cyclohexylbenzene

The cyclohexylbenzene fed to the oxidation step of the process of the present disclosure can be supplied by chemical reactions of certain raw materials, such as those described below (e.g., a hydroalkylation reaction or an alkylation reaction), and/or by recycling of residual cyclohexylbenzene not consumed in subsequent process steps where a cyclohexylbenzene-containing feed is subjected to a chemical reaction, such as oxidation.

The cyclohexylbenzene supplied to the oxidation step can be produced and/or recycled as part of an integrated process for producing phenol and cyclohexanone from benzene. In such an integrated process, benzene is initially converted to cyclohexylbenzene by any conventional technique, including oxidative coupling of benzene to make biphenyl followed by hydrogenation of the biphenyl. However, in practice, the cyclohexylbenzene is desirably produced by contacting benzene with hydrogen under hydroalkylation conditions in the presence of a hydroalkylation catalyst whereby benzene undergoes the following Reaction-1 to produce cyclohexylbenzene (CHB):

(Reaction-1)

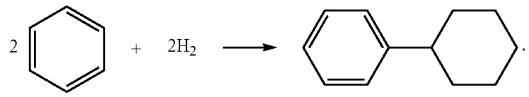

Alternatively, cyclohexylbenzene can be produced by direct alkylation of benzene with cyclohexene in the presence of a solid-acid catalyst such as molecular sieves in the MCM-22 family according to the following Reaction-2:

(Reaction-2)

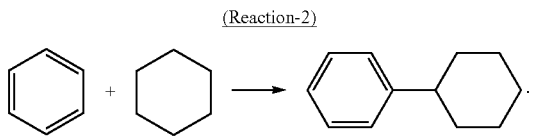

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

The catalyst employed in the hydroalkylation reaction is a bifunctional catalyst comprising a molecular sieve, such as one of the MCM-22 type described above and a hydrogenation metal.

Any known hydrogenation metal may be employed in the hydroalkylation catalyst, specific, non-limiting, suitable examples of which include Pd, Pt, Rh, Ru, Ir, Ni, Zn, Sn, Co, with Pd being particularly advantageous. Desirably, the amount of hydrogenation metal present in the catalyst is from 0.05 wt % to 10.0 wt %, such as from 0.10 wt % and 5.0 wt %, of the total weight of the catalyst.

In addition to the molecular sieve and the hydrogenation metal, the hydroalkylation catalyst may comprise one or more optional inorganic oxide support materials. Suitable inorganic oxide support material(s) include, but are not limited to, clay, non-metal oxides, and/or metal oxides. Specific, non-limiting examples of such support materials include: $SiO_2$, $Al_2O_3$, $ZrO_2$, $Y_2O_3$, $Gd_2O_3$, SnO, $SnO_2$, and mixtures, combinations and complexes thereof.

Although the hydroalkylation and alkylation reactions of benzene can be highly selective towards cyclohexylbenzene, methylcyclopentylbenzene can be produced at a non-negligible amount due to, among others, isomerization of cyclohexene to methylcyclopentene and/or isomerization of cyclohexylbenzene to methylcyclopentylbenzene under the reaction conditions. Depending on the reaction conditions, the concentration of methylcyclopentylbenzene in the hydroalkylation or alkylation reaction product, expressed as the percentage of the weight of methylcyclopentylbenzene relative to the total weight of methylcyclopentylbenzene and cyclohexylbenzene, can be in a range from C1 wt % to C2 wt %, where C1 and C2 can be, independently, 0.01, 0.02, 0.03, 0.04, 0.05, 0.06, 0.07, 0.08, 0.09, 0.10, 0.12, 0.14, 0.15, 0.16, 0.18, 0.20, 0.25, 0.30, 0.35, 0.40, 0.45, 0.50, 0.55, 0.60, 0.65, 0.70, 0.75, 0.80, 0.85, 0.90, 0.95, 1.0, 2, 1.4, 1.5, 1.6, 1.8, 2.0, 2.5, 3.0, 3.5, 4.0, 4.5, 5.0, as long as C1<C2.

Furthermore, the effluent from the hydroalkylation reaction (hydroalkylation reaction product mixture) or from the alkylation reaction (alkylation reaction product mixture) may contain some polyalkylated benzenes, such as dicyclohexylbenzenes (DiCHB), tricyclohexylbenzenes (TriCHB), unreacted benzene, cyclohexane, bicyclohexane, and biphenyl. Thus, typically, after the reaction, the reaction product mixture is separated by distillation to obtain a C6 fraction containing benzene, cyclohexane, a C12 fraction containing cyclohexylbenzene and methylcyclopentylbenzene, and a heavies fraction containing, e.g., C18s such as DiCHBs and C24s such as TriCHBs. The unreacted benzene may be recovered by distillation and recycled to the hydroalkylation or alkylation reactor. The cyclohexane may be sent to a dehydrogenation reactor, with or without some of the residual benzene, and with or without co-fed hydrogen, where it is converted to benzene and hydrogen, which can be recycled to the hydroalkylation/alkylation step.

Depending on the quantity of heavies fraction, it may be desirable to either (a) transalkylate the C18s such as dicyclohexylbenzenes and C24s such as TriCHB with additional benzene or (b) dealkylate the C18s and C24s to maximize the production of the desired monoalkylated species.

Transalkylation with additional benzene is desirably effected in a transalkylation reactor, separate from the hydroalkylation reactor, over a suitable transalkylation catalyst, such as a molecular sieve of the MCM-22 type, zeolite beta, MCM-68 (see U.S. Pat. No. 6,014,018), zeolite Y, zeolite USY, and mordenite. The transalkylation reaction is desirably conducted under at least partially liquid phase conditions, which suitably include a temperature of 100° C. to 300° C., a pressure of 800 kPa to 3500 kPa, a weight hourly space velocity of 1 $hr^{-1}$ to 10 $hr^{-1}$ on total feed, and a benzene/dicyclohexylbenzene weight ratio of 1:1 to 5:1.

Dealkylation is also desirably effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminophosphate, amorphous silica-alumina, an acidic clay, a nixed metal oxide, such as $WO_x/ZrO_2$, phosphoric acid, sulfated zirconia and mixtures thereof. Generally, the acid catalyst includes at least one aluminosilicate, aluminophosphate or silicoaluminophosphate of the EAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction can be from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor can be from about 0.01 to about 10.

The transalkylation or dealkylation product mixture comprising benzene, C12s and heavies can then be separated to obtain a C6 fraction, which comprises primarily benzene and can be recycled to the hydroalkylation/alkylation step, a C12s fraction comprising primarily cyclohexylbenzene and methylcyclopentylbenzene, and a heavies fraction which can be subjected to a transalkylation/dealkylation reaction again or discarded.

It is highly advantageous that one or both of (i) the C12 fraction obtained directly from the hydroalkylation/alkylation reaction product mixture and (ii) the C12 fraction obtained directly from the transalkylation or dealkylation reaction mixture, comprising primarily cyclohexylbenzene and methylcyclopentylbenzene, is subjected to a separation step in which methylcyclopentylbenzene is at least partly (preferably substantially completely) separated and removed from cyclohexylbenzene. As mentioned below, additional sources of cyclohexylbenzene, such as (iii) recycle cyclohexylbenzene stream from the cyclohexylbenzene hydroperoxide concentrator, and/or (iv) recycle cyclohexylbenzene stream from the cleavage reaction product mixture separation step, may be combined with one or more of the C12 fraction (i) or (ii) above and collectively subjected to separation. In this methylcyclopentylbenzene separation step, a purified cyclohexylbenzene stream (the second mixture) comprising methylcyclopentane at a lower concentration than in the C12 feed is obtained.

The C12 teed (the first mixture) to the separation step may contain methylcyclopentylbenzene at a concentration (expressed as the percentage of the weight of methylcyclopentylbenzene relative to the total weight of methylcyclopentylbenzene and cyclohexylbenzene) in a range from C1 wt % to C2 wt %, where C1 and C2 can be, independently, 0.01, 0.02, 0.03, 0.04, 0.05, 0.06, 0.07, 0.08, 0.09, 0.10, 0.12, 0.14, 0.15, 0.16, 0.18, 0.20, 0.25, 0.30, 0.35, 0.40, 0.45, 0.50, 0.55, 0.60, 0.65, 0.70, 0.75, 0.80, 0.85, 0.90, 0.95, 1.0, 1.2, 1.4, 1.5, 1.6, 1.8, 2.0, 2.5, 3.0, 3.5, 4.0, 4.5, 5.0, as long as C1<C2.

As discussed above, among MCPB1, MCPB2cis, MCPB2trans, and MCPB3s, MCPB2cis has the lowest normal boiling temperature, and MCPB2cis has the highest normal boiling temperature. Also, MCPB1, MCPB2trans, and MCPB3s have normal boiling temperatures close to that of cyclohexylbenzene. Thus, in the methylcyclopentylbenzene separation step, MCPB2trans can be preferentially removed, and MCPB2cis may be preferentially retained in the purified cyclohexylbenzene stream, which is then fed to the oxidation step. Thus, it is desirable that the first mixture comprises MCPB2trans at a concentration of C(MCPB2trans)1, expressed as the weight percentage of MCPB2trans based on the total weight of the first mixture, and the second mixture comprises MCPB2trans at a concentration of C(MCPB2trans)2, expressed as the weight percentage of methylcyclopentylbenzene based on the total weight of the second mixture, and R1≤C(MCPBtrans2)1/C(MCPBtrans2)2≤R2, and R1 and R2 can be, independently, 1.2, 1.4, 1.5, 1.6, 1.8, 2, 4, 5, 6, 8, 10, 20, 40, 50, 60, 80, 100, 200, 400, 600, 600, 800, 1000, as long as R1<R2. Further alternatively or additionally, it may be desirable that the first mixture comprises MCPB2cis at a concentration of C(MCPB2cis)1, expressed as the weight percentage of MCPB2cis based on the total weight of the first mixture, and the second mixture comprises MCPB2cis at a concentration of C(MCPB2cis)2, expressed as the weight percentage of methylcyclopentylbenzene based on the total weight of the second mixture, and R3≤C(MCPB2cis)1/C(MCPB2cis)2≤R4, and R3 and R4 can be, independently, 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10, as long as R3<R4. Complete separation of MCPB2cis from cyclohexylbenzene is much more difficult than complete separation of MCPB2trans from cyclohexylbenzene. Therefore, allowing the purified cyclohexylbenzene (the second mixture) to comprise MCPB2cis at a higher concentration than MCPB2trans and at a substantial concentration may significantly reduce the size and energy consumption of the distillation column used to separate methylcyclopentylbenzene from cyclohexylbenzene. Further additionally or alternatively, the methylcyclopentylbenzene concentration in total in the purified cyclohexylbenzene (the second mixture) is desirably reduced compared to the cyclohexylbenzene and methylcyclopentylbenzene-containing C12 feed (the first mixture) fed to the separation step. Thus, where the first mixture comprises methylcyclopentylbenzene at a concentration of C(MCPB)1, expressed as the weight percentage of methylcyclopentylbenzene based on the total weight of the first mixture, and the second mixture comprises methylcyclopentylbenzene at a concentration of C(MCPB)2, expressed as the weight percentage of methyl- cyclopentylbenzene based on the total weight of the second mixture, it is highly desirable that R5≤C(MCPB)1/C(MCPB)2≤R6, where R5 and, R6 can be, independently: 1.2, 1.4, 1.5, 1.6, 1.8, 2, 4, 5, 6, 8, 10, 20, 40, 50, 60, 80, 100, 200, 400, 600, 600, 800, 1000, as long as R5<B6.

Because cyclohexylbenzene has a higher boiling point than the methylcyclopentylbenzene isomers, the purified cyclohexylbenzene is typically obtained at a location in proximity to the bottom of the distillation column, and the methylcyclopentylbenzene-rich fraction is obtained at a location in proximity to the top of the column. The purified cyclohexylbenzene (the second mixture) may contain methylcyclopentylbenzene at a total concentration in a range from C3 ppm to C4 ppm, where C3 and C4 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 5000, as long as C3<C4. Additionally or alternatively, the purified cyclohexylbenzene may contain MCPB2trans at a total concentration in a range from C5 ppm to C6 ppm, where C5 and C6 can be, independently, 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C5<C6. Further additionally or alternatively, the purified cyclohexylbenzene may contain MCPB2cis at a total concentration in a range from C7 ppm to C8 ppm, where C7 and C8 can be, independently, 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C7<C8. Further additionally or alternatively, the purified cyclohexylbenzene may contain MCPB3s at a total concentration in a range from C9a ppm to C9b ppm, where C9a and C9b can be, independently, 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C9a<C9b. Further additionally or alternatively, the purified cyclohexylbenzene may contain MCPB1 at a total concentration in a range from C10a ppm to C10b ppm, where C10a and C10b can be, independently, 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C9a<C9b. Further additionally or alternatively, the purified cyclohexylbenzene may contain MCPB2cis at a total concentration of C(MCPB2cis) and MCPB2trans at a concentration of C(MCPB2trans), and r1≤C(MCPB2cis)/C(MCPB2trans), preferably r1≤C(MCPB2cis)/C(MCPB2trans)≤r2, where r1 and r2 can be, independently, 1.5, 2.0, 2.5, 3.0, 3.5, 4.0, 4.5, 5.0, 6.0, 7.0, 8.0, 9.0, 10, 20, 30, 40, 50, 60, 70, 80, 90, 100, 200, 400, 500, 600, 800, 1000, as long as r1<r2. Further additionally or alternatively, the purified cyclohexylbenzene may contain MCPB3s at a total concentration of C(MCPB3) and MCPB2trans at a concentration of C(MCPB2trans), and r3≤C(MCPB3)/C(MCPB2trans), preferably r3≤C(MCPB3)/C(MCPB2trans)≤r4, where r3 and r4 can be, independently, 2.0, 2.5, 3.0, 3.5, 4.0, 4.5, 5.0, 6.0, 7.0, 8.0, 9.0, 10, 20, 30, 40, 50, 60, 70, 80, 90, 100, 200, 400, 500, 600, 800, 1000, as long as r3<r4.

The purified cyclohexylbenzene (the second supplied to the oxidizing step may comprise cyclohexylbenzene at a concentration in a range from CON1 wt % to CON2 wt %, based on the total weight of the feed introduced into the oxidation reactor, where CON1 and CON2 can be, independently, 10, 20, 30, 40, 50, 60, 70, 80, 90, 92, 94, 95, 96, 97, 98, 99, 99.5, or even 99.9, or even higher, as long as CON1<CON2.

The cyclohexylbenzene composition comprising methylcyclopentylbenzene, especially the purified cyclohexylbenzene composition before being fed to the oxidizing step containing methylcyclopentylbenzene (especially MCPB2trans) at a low level, also constitute an aspect of the present invention. As discussed below, the purified cyclohexylbenzene composition with low concentration of methylcyclopentylbenzene can be advantageously used for making high purity phenol and cyclohexanone with reduced need for purification compared to processes using non-purified cyclohexylbenzene with higher methylcyclopentylbenzene concentration as the feed.

As will be discussed later, the inclusion of the step of separating at least a portion of methylcyclopentylbenzene from cyclohexylbenzene before it is fed to oxidation can have significant advantages especially in terms of final cyclohexanone purification, phenol purification and the product purity of these two major products.

One or more of the cyclohexylbenzene sources (i), (ii), (iii), and (iv) above may contain olefins, such as cyclohexenylbenzenes at non-negligible concentration(s). The olefin(s) can be produced during the hydroalkylation step, the oxidizing step, and/or the cleavage step. We have learned that the presence of olefin in the cyclohexylbenzene feed (the second mixture) to the oxidation step can be detrimental to the oxidation catalyst (such as NHPI, described below). As such, one or more of these cyclohexylbenzene-source materials may be subjected to a step of hydrogenation in the presence of a hydrogenation catalyst comprising a precious metal such as Pd, Pt, Ru, Th, Rh, and the like, prior to or after the separation step where methylcyclopentylbenzene is at least partly separated and removed from the cyclohexylbenzene fed to the oxidizing step. Preferably, the hydrogenation is conducted before the methylcyclopentylbenzene separation step.

In addition to cyclohexylbenzene and methylcyclopentylbenzene, the feed to the oxidizing step (the second mixture) may contain, based on the total weight of the feed, one or more of the following: (i) bicyclohexane at a concentration in a range from at 1 ppm to 1 wt %, such as from 10 ppm to 8000 ppm; (ii) biphenyl at a concentration in a range from 1 ppm to 1 wt %, such as from 10 ppm to 8000 ppm; (iii) water at a concentration up to 5000 ppm, such as from 100 ppm to 1000 ppm; and (iv) olefins or alkene benzenes, such as phenylcyclohexene, at a concentration no greater than 1000 ppm.

Oxidation of Cyclohexylbenzene

The purified cyclohexylbenzene (second mixture) described above is then fed to the oxidizing step (step (III) or step (B) as described in the present disclosure), which can be conducted in one or more oxidation reactor(s). In the oxidation reactor(s), at least a portion of the cyclohexylbenzene contained in the oxidation feed is converted to cyclohexyl-1-phenyl-1-hydroperoxide, the desired hydroperoxide, according to the following Reaction-3:

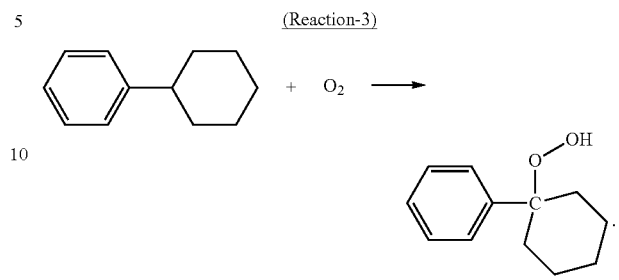

Methylcyclopentylbenzene, if present in the cyclohexylbenzene feed, is likewise oxidized to the corresponding hydroperoxide according to Reaction-4:

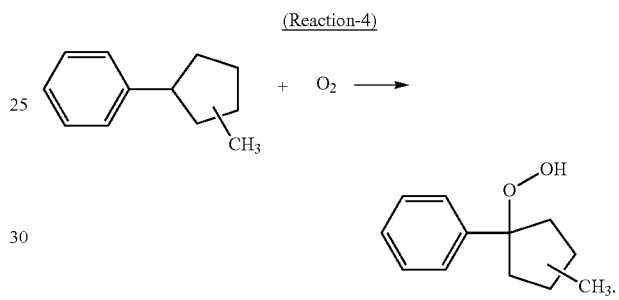

It has been found, in a surprising manner, that MCPB2cis undergoes Reaction-3 at a much higher rate than MCPB2trans. Thus, assuming (i) that the cyclohexylbenzene feed to the oxidizing step comprises MCPB2trans and MCPB2cis at the same concentration, and (ii) both of the oxidation of MCPB2trans and MCPBcis are kinetics-driven, in the oxidation reaction product mixture, the concentration of MCPB2trans is likely higher than MCPB2cis.

The feed to the oxidizing step may also contain phenol since phenol can be a non-negligible by-product of the cyclohexylbenzene oxidation reaction. Hence, if not abated, phenol will be present in the residual cyclohexylbenzene recycled from the oxidation reaction mixture (the third mixture) and possibly the cleavage reaction product mixture. However, it is believed that the presence of phenol in the oxidation feed can inhibit the oxidation reaction and hence, the level of phenol in the oxidation feed (the second mixture) is desirably no greater than 50 ppm, desirably no greater than 10 ppm, based on the total weight of the feed. Preferably, the oxidation feed (e.g., the second mixture) contains no detectable phenol.

In exemplary processes, the oxidizing step may be accomplished by contacting an oxygen-containing gas, such as air and various derivatives of air, with the feed comprising cyclohexylbenzene. For example, a stream of $O_2$, pure air, or other $O_2$-containing mixtures can be pumped through the cyclohexylbenzene-containing feed in an oxidation reactor such as a bubble column to effect the oxidation.

The oxidation may be conducted in the absence or presence of a catalyst. Examples of suitable oxidation catalysts include those having a structure of formula (FC-I), (FC-II), or (FC-III) below:

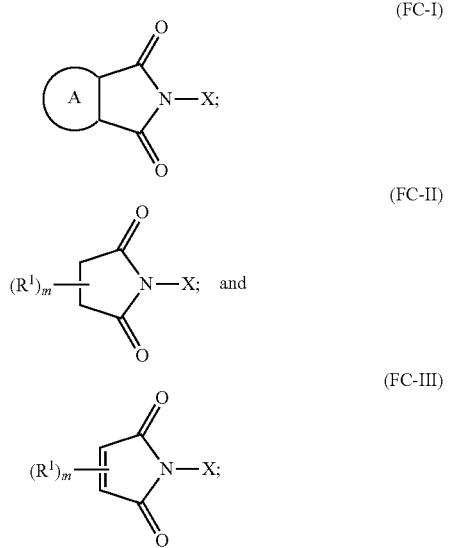

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

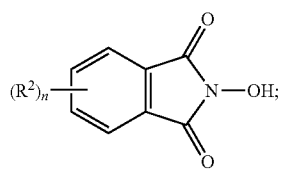

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxy phthalic imide). For example, the feed to oxidizing step can comprise from 10 to 2500 ppm of NHPI by weight of the cyclohexylbenzene in the feed.

Non-limiting examples of suitable reaction conditions of the oxidizing step include a temperature from 70° C., to 200° C., such as 90° C., to 130° C., and a pressure of 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series, each operating at the same or different conditions selected to enhance the oxidation reaction of reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as a byproduct of the oxidation reaction of cyclohexylbenzene, or as the oxidation reaction product mixture of some oxidizable component other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration of at most 5.0 wt %, such as at most 3.0 wt %, 2.0 wt %, 1.0 wt %, or even 0.1 wt %. They are undesirable because they may not convert into phenol and cyclohexanone in the cleavage reaction at the desired conversion and/or selectivity, resulting in overall yield loss. The inclusion of the step of methylcyclopentylbenzene separation and removal from the cyclohexylbenzene feed to oxidation can significantly reduce the amount of methylcyclopentylbenzene hydroperoxide(s) in the oxidation reaction mixture.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water because: (i) depending on the production method and source, the cyclohexylbenzene fed to the oxidizing step can contain water at a certain level; and (ii) during the oxidation reaction, water is produced due to, inter alia, premature decomposition of the hydroperoxides produced. While a portion of the water contained in the reaction media in the oxidizing step can be carried away if a stream of gas passes through the oxidation reaction medium and exits the oxidation reactor, some water will remain in the oxidation reaction product mixture. The concentration of water in the oxidation reaction product mixture exiting the oxidation reactor is C1a ppm by weight, based on the total weight of the oxidation reaction product mixture, which can range from C1a ppm to C1b ppm, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

As mentioned above, the oxidation reaction product mixture may comprise methylcyclopentylbenzene at a concentration in a range from C9 ppm to C10 ppm, based on the total weight of the oxidation reaction product mixture, where C9 and C10 can be, independently, 0.001, 0.005, 0.01, 0.05, 0.10, 0.50, 1.0, 5.0, 10, 50, 100, 200, 300, 400, or 500. Additionally or alternatively, the oxidation reaction product mixture (the third mixture) may comprise MCPB2trans at a concentration in a range from C11 ppm to C12 ppm, based on the total weight of the oxidation reaction product mixture, where C11 and C12 can be, independently, 0.001, 0.005, 0.01, 0.05, 0.10, 0.50, 1.0, 5.0, 10, 50, 100, 200, 300, 400, or 450, as long as C11<C12.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment the Oxidation Reaction Product Mixture

In the process of the present disclosure, before being supplied to the cleavage step, at least a portion of the oxidation reaction product mixture may be separated into at least a first fraction comprising cyclohexyl-1-phenyl-1-hydroperoxide and a second fraction comprising cyclohexylbenzene, methylcyclopentylbenzene and possibly phenol. The first fraction typically has a higher concentration of cyclohexyl-1-phenyl-1-hydroperoxide than the second fraction. The second fraction typically has a higher concentration of cyclohexylbenzene than the first fraction.

The separation process may include subjecting at least a portion of the oxidation reaction product mixture to vacuum evaporation so as to recover a vapor phase comprising a major portion of the cyclohexylbenzene, methylcyclopentylbenzene, phenol, if any, and other lower boiling components of the oxidation reaction product mixture portion. For example, water, if present in the oxidation reaction product mixture portion, will preferentially partition with the cyclohexylbenzene and phenol in the vapor phase. The majority of the cyclohexyl-1-phenyl-1-hydroperoxide and other higher boiling components of the oxidation reaction product mixture portion, such as other hydroperoxides and catalyst, if present in the oxidation reaction product mixture portion, will preferentially remain in the liquid phase first fraction. The vapor phase is then condensed to produce the desired second fraction in liquid phase.

Where vacuum evaporation is used to effect separation of the oxidation reaction product mixture, the first fraction may have a composition comprising:

1) cyclohexyl-1-phenyl-1-hydroperoxide at a concentration in a range from Chp3 wt % to Chp4 wt %, based on the total weight of the first fraction, where Chp3 and Chp4 can be, e.g., independently, 45, 50, 55, 60, 65, 70, 75, 80, 85, 90, as long as Chp3 Chp4;

2) cyclohexylbenzene at a concentration in a range from Cchb3 wt % to Cchb4 wt %, based on the total weight of the first fraction, where Cchb3 and Cchb4 can be, independently, 10, 15, 20, 25, 30, 35, 40, 45, 50, 55, as long as Cchb3<Cchb4;

3) phenol at a concentration of CPh3 ppm to CPh4 ppm, where CPh3 and CPh4 can be, independently: 0, 5, 10, 15, 20, 25, 30, 40, 50, 100, as long as CPh3<CPh4; and 4) water at a concentration of C2a ppm to C2b ppm, where C2a and C2b can be, independently: 0, 5, 10, 15, 20, 25, 30, 35, 40, 45, as long as C2a<C2b.

The second fraction may have a composition comprising:

1) cyclohexylbenzene at a concentration in a range from Cchb5 wt % to Cchb6 wt %, based on the total weight of the second fraction, where Cchb5 and Cchb6 can be, independently, 85, 86, 87, 88, 89, 90, 93, 95, 99, as long as Cchb5<Cchb6;

2) methylcyclopentylbenzene at various concentrations, depending on whether methylcyclopentylbenzene is removed in a separation and removal step before oxidation;

3) phenol at a concentration of CPh5 ppm to CPh6 ppm, based on the total weight of the second fraction, where CPh5 and CPh6 can be, independently: 100, 150, 200, 250, 300, 350, 400, 450, 500, 550, 600, 650, 700, 750, 800, 850, 900, 950, 1000, 1500, 2000, as long as CPh5<CPh6; and 4) cyclohexyl-1-phenyl-1-hydroperoxide at a concentration in a range from Chp5 wt % to Chp6 wt %, based on the total weight of the second fraction, where Chp5 and Chp6 can be, independently: 0, 0.1, 0.5 1, 1.5, 2, 2.5 5, 7.5, 10, as long as Chp5<Chp6.

Desirably, the concentration of cyclohexyl-1-phenyl-1-hydroperoxide in the first fraction can be at least 50 wt %, while the concentration of cyclohexylbenzene in the first fraction is at most 50 wt %, both concentrations being based on the total weight of the first fraction.

Advantageously, the concentration of cyclohexyl-1-phenyl-1-hydroperoxide in the second fraction can be at most 5 wt %, while the concentration of cyclohexylbenzene in the second fraction can be at least 95 wt %, both concentrations being based on the total weight of the second fraction.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in orange from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture portion into first and second fractions, part or all of the first fraction can be routed directly to the cleavage step. Thus, although water can be detrimental to the cleavage step, the concentration of water in the first fraction remaining after the vacuum evaporation is typically sufficiently low to obviate the need for further water reduction. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

In accordance with the present process, the second fraction produced from the oxidation reaction product mixture is treated to reduce the level of phenol therein before part or all of the cyclohexylbenzene in the second fraction is recycled to the hydrogenation, methylcyclopentylbenzene removal and/or the oxidizing step.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, of one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

As discussed above, the present process also includes the step of cleaving at least a portion of the cyclohexylbenzene hydroperoxide contained in the oxidation reaction product mixture in the presence of an acid catalyst to produce a cleavage product mixture comprising the acid catalyst, phenol, cyclohexanone, methylcyclopentanone, cyclohexylbenzene, and methylcyclopentylbenzene. As used herein, "cleaving" means causing a cleavage reaction to occur. In the cleavage reaction, at least a portion of the cyclohexyl-1-phenyl-1-hydroperoxide decomposes in high selectivity to cyclohexanone and phenol, and further, other hydroperoxides present may decompose to form various products, discussed below. As a specific example, methylcyclopentylbenzene hydroperoxide can cleave to form phenol and methylcyclopentanone.

The acid catalyst can be at least partially soluble in the cleavage reaction mixture, is stable at a temperature of at least 185° C. and has a lower volatility (higher normal boiling point) than cyclohexylbenzene. The acid catalyst can be also at least partially soluble in the cleavage product mixture.

Acid catalysts include, but are not limited to, Bronsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

The cleavage reaction occurs under cleavage conditions including a temperature of at least 20° C. and no greater than 200° C., or at least 40° C. and no greater than 120° C., and a pressure of at least 1 and no greater than 370 psig (at least 7 kPa, gauge and no greater than 2,550 kPa, gauge), or at least 14.5 psig and no greater than 145 psig (at least 100 kPa, gauge and no greater than 1,000 kPa, gauge) such that the cleavage reaction mixture is completely or predominantly in the liquid phase during the cleavage reaction.

The cleavage reaction mixture can contain the acid catalyst at a concentration in a range from Cac1 ppm to Cac2 ppm by weight of the total weight of the cleavage reaction mixture, where Cac1 and Cac2 can be, independent 20, 30, 40, 50, 60, 80, 100, 150, 200, 250, 300, 350, 400, 450, 500, 600, 700, 800, 900, 1000, 1500, 2000, 2500, 3000, 3500, 4000, 4500, or even 5000, as long as Cac1<Cac2. Preferably, Cac1 is 50, and Cac2 is 200.

Conversion of hydroperoxides, such as cyclohexyl-1-phenyl-1-hydroperoxide, and conveniently all cyclohexyl-1-phenyl-1-hydroperoxide and other hydroperoxides, may be very high in the cleavage reaction, e.g., at least 90.0 wt %, or at least 95.0 wt %, or at least 98.0 wt %, or at least 99.0 wt %, or at least 99.5 wt %, or at least 99.9 wt %, or even 100 wt %, the percentage conversion based on the weight of a given hydroperoxide, or of all hydroperoxides present in the portion of the first fraction undergoing the cleavage reaction. This is desirable because any hydroperoxide, even the cyclohexyl-1-phenyl-1-hydroperoxide, becomes a contaminant in the cleavage product mixture and treated cleavage product mixture, discussed below. Hydroperoxides cause undesired chemistry when decomposed under uncontrolled conditions outside the cleavage reaction, or if thermally decomposed under the conditions in a distillation column.

The major products of the cleavage reaction of cyclohexyl-1-phenyl-1-hydroperoxide are phenol and cyclohexanone according to the following desired Reaction-5:

(Reaction-5)

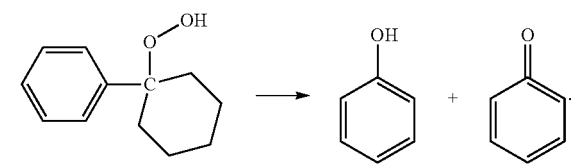

Similarly, methylcyclopentyl-1-phenyl-1-hydroperoxide can undergo the following cleavage Reaction-6 to produce phenol and methylcyclopentanone:

(Reaction-6)

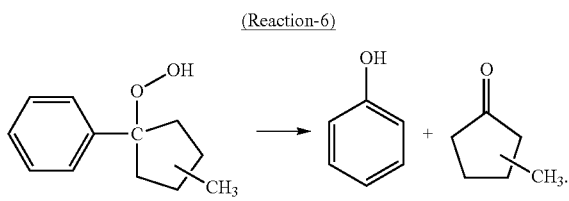

Desirably, each mole of cyclohexyl-1-phenyl-1-hydroperoxide produces one mole of phenol and one mole of cyclohexanone. However, due to side reactions, the selectivity of the cleavage reaction to phenol can range from Sph1% to Sph2% and the selectivity to cyclohexanone can range from Sch1% to Sch2%, where Sph1, Sph2, Sch1, and Sch2 can be, independently, 87, 88, 89, 90, 91, 92, 93, 94, 95, 96, 97, 98, 99 or even 99.5, as long as Sph1<Sph2, and Sch1<Sch2.

Besides the cleavage feed comprising cyclohexylbenzene hydroperoxide, cyclohexylbenzene and other components originating directly from the oxidation reaction product mixture, the cleavage reaction mixture may further comprise other added materials, such as the cleavage catalyst, a solvent, and one or more products of the cleavage reaction such as phenol and cyclohexanone recycled from the cleavage product mixture, or from a downstream separation step. Thus, the cleavage reaction mixture inside the cleavage reactor may comprise, based on the total weight of the cleavage reaction mixture: (i) phenol at a concentration from CPh9 wt % to CPh10 wt %, where CPh9 and CPh10 can be, independently, 20, 25, 30, 35, 40, 45, 50, 55, 60, 65, 70, 75, or 80, as long as CPh9<CPh10; (ii) cyclohexanone at a concentration from Cch1 wt % to Cch2 wt %, where Cch1 and Cch2 can be, independently, 20, 25, 30, 35, 40, 45, 50, 55, 60, 65, 70, 75, or 80, as long as Cch1<Cch2; (iii) cyclohexylbenzene at a concentration from Cchb7 wt % to Cchb8 wt %, where Cchb7 and Cchb8 can be, independently, 5, 8, 9, 10, 12, 14, 15, 18, 20, 22, 24, 25, 26, 28, 30, 35, 40, 45, 50, 55, 60, 65, 70, as long as Cchb7<Cchb8; and (iv) methylcyclopentylbenzene and methylcyclopentanone at various concentrations depending on whether a methylcyclopentylbenzene separation and removal step is conducted for the cyclohexylbenzene feed prior to oxidation.

As used herein, a "contaminant" or a "contaminant byproduct" may include any unwanted hydrocarbon or oxygenated hydrocarbon component in the cleavage product mixture or the neutralized cleavage product mixture, or any portion of either; that is anything other than phenol, cyclohexanone, and cyclohexylbenzene. They are unwanted because their presence indicates a decreased yield of desired product phenol and cyclohexanone from cyclohexylbenzene, or they cause difficulties in the separation and purification of phenol, cyclohexanone or unconverted cyclohexylbenzene, or some combination thereof. A contaminant in the cleavage product mixture or the neutralized cleavage product mixture, or any portion thereof may have been produced in any step of the present process, or may have been contained in the teed comprising cyclohexylbenzene undergoing oxidation. For example, a contaminant may be present in the cleavage product mixture as a result of one or more of (i) it was included with the cyclohexylbenzene (e.g., as a byproduct of production using hydroalkylation or alkylation); (ii) it was produced in oxidation of the feed comprising cyclohexylbenzene, and potentially the oxidation of an oxidizable component from (i); and/or (iii) it was produced in the cleavage reaction of at least a portion of the oxidation reaction product mixture from (ii).

The reactor used to effect the cleavage reaction (i.e., the cleavage reactor) may be any type of reactor known to those skilled in the art. For example, the cleavage reactor may be a simple, largely open vessel operating in a near-continuous stirred tank reactor mode, or a simple, open length of pipe operating in a near-plug flow reactor mode. The cleavage reactor may comprise a plurality of reactors in series, each performing a portion of the conversion reaction, optionally operating in different modes and at different conditions selected to enhance the cleavage reaction at the pertinent conversion range. The cleavage reactor can be a catalytic distillation unit.

The cleavage reactor can be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) can be used to at least a part of the heat generated.

The cleavage product mixture exiting the cleavage reactor may comprise, based on the total weight of the cleavage product mixture: (i) phenol at a concentration from CPh11 wt % to CPh12 wt %, where CPh11 and CPh12 can be, independently, 20, 25, 30, 35, 40, 45, 50, 55, 60, 65, 70, 75, or 80, as long as Ch11<CPh12, (ii) cyclohexanone at a concentration from Cch3 wt % to Cch4 wt %, where Cch3 and Cch4 can be, independently, 20, 25, 30, 35, 40, 45, 50, 55, 60, 65, 70, 75, or 80, as long as Cch3<Cch4; (iii) cyclohexylbenzene at a concentration from Cchb9 wt % to Cchb10 wt %, where Cchb9 and Cchb10 can be, independently, 5, 8, 9, 10, 12, 14, 15, 18, 20, 22, 24, 25, 26, 28, 30, 35, 40, 45, 50, 55, 60, 65, 70, as long as Cchb9<Cchb10; (iv) methylcyclopentanone and methylcyclopentylbenzene at various concentrations depending on whether a step of removing methylcyclopentylbenzene is carried out for the cyclohexylbenzene feed before oxidation.

Separation and Purification

As discussed above, the cleavage product mixture may comprise one or more contaminants. In embodiments disclosed herein, the processes further comprise contacting at least a portion of a contaminant with an acidic material to convert at least a portion of the contaminant to a converted contaminant, thereby producing a modified product mixture. Detailed description of the contaminant treatment process can be found, e.g., in international Publication WO2012/036822A1, the relevant content of which is incorporated herein by reference in its entirety.

At least a portion of the cleavage product mixture may be subjected to a neutralization reaction, which may include all or some fraction of the cleavage product mixture as directly produced without undergoing any separation. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first distillation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone and at least some of the methylcyclopentylbenzene is obtained. Given the close boiling points of cyclohexylbenzene, MCPB2cis, MCPB3s and MCPB1, as mentioned above, some or all of these methylcyclopentylbenzene isomers may be included in the cyclohexylbenzene side fraction. As to MCPB2trans, because it tends to have a strong affinity with phenol, at least part of it will become a contaminant in the upper fraction comprising phenol and cyclohexanone.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation and/or a hydrogenation step as disclosed in, for example, WO2011/100013A1, the entire contents of which are incorporated herein by reference. Furthermore, depending on the concentration of methylcyclopentylbenzene in the cyclohexylbenzene fraction, it may or may not be subjected to methylcyclopentylbenzene removal before recycled to the oxidizing step.

The fraction comprising phenol, cyclohexanone, methylcyclopentanone, and methylcyclopentylbenzene can be further separated by simple distillation to obtain an upper fraction comprising primarily cyclohexanone and methylcyclopentanone and a lower stream comprising primarily phenol, some cyclohexanone, and some methylcyclopentylbenzene (and possibly some cyclohexylbenzene). Cyclohexanone cannot be completely separated form benzene due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol, the extractive solvent and methylcyclopentylbenzene can be obtained. In a subsequent distillation column, the lower fraction can then be separated to obtain an upper fraction comprising a phenol product and a lower fraction comprising the extractive solvent. Depending on the extent of methylcyclopentylbenzene removal in an upstream step, such as before oxidation, concentration of methylcyclopentylbenzene, especially MCPB2trans, may be still high in the phenol product thus obtained. To further reduce concentration of methylcyclopentylbenzene from the phenol product, if necessary, an additional step of extractive distillation may be conducted, where a stream of an extractive solvent (e.g., a glycol mentioned above for the extractive distillation of the mixture comprising phenol and cyclohexanone, which may be the same or different) can be injected to the middle section of the distillation column to break the MCPB2trans/phenol azeotropic or other non-ideal mixture, thereby obtaining an upper fraction comprising pure phenol and a lower fraction comprising methylcyclopentylbenzene (especially MCPB2trans) and the extractive solvent. The methylcyclopentylbenzene/solvent mixture may be subjected to further separation to obtain a pure methylcyclopentylbenzene (especially MPCB2trans) product, which can find use as a specialty chemical.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6.

The phenol produced through the processes disclosed herein may be used for example, to produce phenolic resins, bisphenol A, ε-caprolactam, adipic acid, and/or plasticizers.

Description According to the Drawing

FIG. 1 is a schematic flow sheet showing a process/system 1001 for making phenol and cyclohexanone starting from benzene hydroalkylation. In this process, a hydrogen sub-stream 1003a from main hydrogen supply stream 1003 is mixed with a benzene sub-stream 1005a from main benzene supply stream 1005, and then fed into a hydroalkylation reactor 1007, where the mixture contacts a fixed bed of hydroalkylation catalyst 1008 comprising a MCM-22 family molecular sieve and a precious metal hydrogenation component. Residual hydrogen stream 1009 exits the hydroalkylation reactor 1007 in the vicinity of the bottom. The hydroalkylation reaction product mixture 1011, comprising residual benzene, cyclohexylbenzene, methylcyclopentylbenzene, cyclohexane, DiCHB, and possibly TriCHB and other components, is then fed to a distillation column 1013, where a C6 stream comprising benzene and cyclohexane is obtained in the vicinity of the top, a heavies stream 1017 comprising DiCHB, TriCHB, and the like, is obtained in the vicinity of the bottom, and a C12 stream 1016 comprising cyclohexylbenzene and methylcyclopentylbenzene is obtained in the middle. The C6 stream can be separated to obtain a benzene stream, which can be recycled to benzene source 1005, and a cyclohexane stream, which can be sent to a dehydrogenator (not shown), where it is converted into benzene and hydrogen, which can be recycled to the benzene source 1005 and the hydrogen source 1003, respectively. The heavies stream 1017 is then fed to a transalkylation reactor 1019 together with a benzene substream 1005b, where at least a portion of the DiCHB and TriCHB are converted to cyclohexylbenzene. The transalkylation reaction product mixture stream 1023, comprising cyclohexylbenzene, benzene, DiCHB and TriCHB, is then fed into a distillation column 1031, where a C6 stream 1033 comprising residual benzene is obtained in the vicinity of the top, which may be recycled to the benzene source 1005, a heavies stream 1035 comprising C18 and other heavy components is obtained in the vicinity of the bottom, which may be partly recycled back to the transalkylation reactor 1019, and a C12 stream 1037 comprising cyclohexylbenzene and methylcyclopentylbenzene is obtained in the middle.

The C12 stream 1037 from the distillation column 1031, the C12 stream 1016 from distillation column 1013, and recycle C12 stream 1081 (combination of recycle C12 streams 1059 and 1077, described below), are combined and delivered to a hydrogenation reactor 1041 together with a hydrogen sub-stream 1003b from hydrogen source 1003. In reactor 1041, at least a portion of the olefin(s) present in the C12 streams from the various sources, and possibly certain oxygenates, react with hydrogen in contacting a fixed catalyst bed 1042 comprising a precious metal hydrogenation component. A side stream 1043 comprising residual hydrogen may exit the reactor 1041 and recycled to hydrogen source 1003 upon cleaning. The hydrogenated C12 stream 1044, consisting essentially of cyclohexylbenzene and methylcyclopentylbenzene, is then fed into a distillation column 1045, where an upper stream 1047 comprising primarily methylcyclopentylbenzene is obtained, and a lower stream 1048 comprising primarily purified cyclohexylbenzene is obtained. It should be noted, however, that some of the methylcyclopentylbenzene isomers, such as MCPB2cis and MCPB3s, can be present in stream 1048 due to their close boiling points to that of cyclohexylbenzene. MCPB2trans, however, will primarily and preferably substantially completely separated from stream 1048, and primarily and preferably completely included in stream 1047.

The purified cyclohexylbenzene stream 1048 is then fed into an oxidation reactor 1051, where it contacts a stream of air 1049 fed through the bottom thereof in the presence of NHPI as an oxidation catalyst. Spent air stream 1053 exits the oxidation reactor 1051 from the top. The resultant oxidation reaction product mixture 1055, comprising cyclohexylbenzene hydroperoxide, cyclohexylbenzene, methylcyclopentylbenzene, and methylcyclopentylbenzene hydroperoxide, is then delivered to a cyclohexylbenzene hydroperoxide concentrator 1057, where an upper stream 1059 comprising primarily cyclohexylbenzene (and possibly a small amount of methylcyclopentylbenzene) is obtained from the top, and a lower stream 106 comprising cyclohexylbenzene hydroperoxide at a higher concentration than in 1055, cyclohexylbenzene at a concentration lower than in 1055, methylcyclopentylbenzene hydroperoxide, and methylcyclopentylbenzene, is obtained in the vicinity of the bottom thereof. The upper stream 1059, called a recycle cyclohexylbenzene stream, can then be purified by, e.g., washing, and then recycled as part of the stream 1081 to the hydrogenation reactor 1041, described above.

The lower stream 1061 comprising cyclohexylbenzene hydroperoxide and methylcyclopentylbenzene hydroperoxide at concentrations higher than in stream 1055 is then fed into a cleavage reactor 1063, where it is mixed with a sulfuric acid stream 1065, undergoes a cleavage reaction, and exits the cleavage reactor 1063 as a cleavage reaction product mixture 1067 comprising sulfuric acid, phenol, cyclohexanone, methylcyclopentanone, cyclohexylbenzene, methylcyclopentylbenzene, and olefins, which is then divided into a recycle stream 1067a and a product stream 1067b. The recycle stream 1067a is then recycled back to the cleavage reactor 1063, which also serves as a diluent of the cleavage feed 1061.

To the cleavage product stream 1067b is then injected a stream of diamine 1071 from a storage tank 1069, which reacts with sulfuric acid to form a salt. The thus neutralized product stream 1072 is then fed into a distillation column 1073, where a lower stream 1075 comprising heavies such as the diamine sulfate salt is obtained in the vicinity of the bottom, a upper stream 1079 comprising phenol, cyclohexanone, methylcyclopentanone, methylcyclopentylbenzene, and possibly cyclohexylbenzene at a small concentration in the vicinity of the top is obtained, and a middle stream 1077 comprising cyclohexylbenzene, methylcyclopentylbenzene and olefins such as cyclohexenylbenzene is obtained. As discussed above, while the various isomers of methylcyclopentylbenzene and cyclohexylbenzene have the same empirical chemical formula, they have quite different normal boiling points, and they tend to behave differently in chemical reactions and physical distillation operations. For example, it has been surprisingly found that MCPB2trans has a much lower boiling point than MCPB2cis, and that MCPB2trans tends to contaminate the phenol stream, even though these two compounds (phenol and MCPB2trans) have quite different normal boiling points. Without intending to be bound by a particular theory, it is believed that this is due to a non-ideal mixture (e.g., azeotrope) formed between MCPB2trans with phenol. On the other hand, it was surprisingly found that MCPB1, MCPB2cis and MCPB3s do not form azeotropes with phenol. Therefore, the upper stream 1079, which comprises phenol, tends to comprise MCPB2trans at a concentration higher than MCPB2cis and MCPB3s, while the middle stream 1077 can comprise, in addition to cyclohexylbenzene, MCPB1, MCPB3s, MCPB2cis, and MCPB2trans. The middle stream 1077, considered a cyclohexylbenzene recycle stream, can then be combined with another cyclohexylbenzene recycle stream 1059 (described above), and fed into hydrogenation reactor 1042 together with the cyclohexylbenzene streams 1016 and 1037 and a stream of hydrogen 1007b, where at least a portion, preferably all, olefins contained therein is converted into corresponding alkane.

The upper stream 1079, comprising phenol, cyclohexane, methylcyclopentanone, methylcyclopentylbenzene (especially MCPB2trans), is then fed into distillation column 1083, where an upper stream 1085 comprising cyclohexanone and methylcyclopentanone is obtained in the vicinity of the top, and a lower stream 1087 comprising phenol, cyclohexanone and methylcyclopentylbenzene (and possibly cyclohexylbenzene at a small concentration) is obtained in the vicinity of the bottom. Phenol and cyclohexanone form an azeotrope comprising about 28 wt % of cyclohexanone and 72 wt % phenol under normal conditions. Thus, a simple distillation operation without the use of an extractive solvent cannot completely separate a mixture of cyclohexanone and phenol. The upper stream 1085 is then fed into distillation column 1084, where a lower stream 1088 consisting essentially of purified cyclohexanone is obtained in the vicinity of the bottom, and an upper stream 1086 comprising methylcyclopentanone is obtained in the vicinity of the top. The upper stream 1086 may be then further purified to obtain a pure methylcyclopentanone product, which can be used as a valuable solvent, for example. The lower methylcyclopentanone stream 1088 may be further purified by additional chemical and/or physical means depending on the purity requirements of the end applications.

The lower stream 1087 comprising phenol, cyclohexanone, and methylcyclopentylbenzene exiting column 1083 is then fed into an extractive column 1091 together with a stream of diethylene glycol (DEG) from storage tank 1089, where an upper stream 1093 comprising pure cyclohexanone is obtained in the vicinity of the top, and a lower stream 1094 comprising phenol, methylcyclopentylbenzene (and possibly cyclohexylbenzene at a low concentration), and DEG and essentially free of cyclohexanone is obtained in the vicinity of the bottom. The stream 1094 is then fed into a distillation column 1095, where an upper stream 1097 comprising phenol and methylcyclopentylbenzene is obtained in the vicinity of the top, and a bottom stream 1099 consisting essentially of DEG is obtained in the vicinity of the bottom. The crude phenol stream 1097 is then fed into an extractive distillation column 1101 together with a stream of extractive solvent DEG from storage tank 1089 fed into the middle section of the distillation column, where an upper stream 1103 consisting essentially of purified phenol is obtained in the vicinity of the top of the column, and a lower stream 1105 comprising methylcyclopentylbenzene (primarily MCPB2trans) and DEG is obtained in the vicinity of the bottom. The phenol stream 1103 may be further purified by additional chemical and/or physical means depending on the purity requirements of the end applications. The lower stream 1105 is then fed into a distillation column 1107, where an upper stream 1109 comprising methylcyclopentylbenzene (primarily MCPB2trans) is obtained in the vicinity of the top, and a lower stream 1111 comprising DEG is obtained. The lower streams 1099 and 1111, comprising primarily DEG, may be purified and then recycled to storage tank 1089 as appropriate. The stream 1109 may be further purified, where necessary, to harvest a purified methylcyclopentylbenzene (primarily MCPB2trans), which can be used for other applications, such as production of methylcyclopentanone and phenol.

In the above example illustrated in FIG. 1, due to the presence of the distillation column 1045, a great majority (preferably essentially all) of methylcyclopentylbenzene, especially MCPB2trans, is removed from the cyclohexylbenzene fed into the oxidation reactor 1051. As a result, a small amount, if any of all, of methylcyclopentylbenzene hydroperoxide is produced in the oxidation reactor 1051. Consequently, very low concentrations of methylcyclopentanone and methylcyclopentylbenzene are present in the cleavage reaction product mixture 1067b. As a result, the cyclohexanone stream 1085 may comprise methylcyclopentanone at a very low concentration and may therefore be saleable as a pure cyclohexanone product for use in caprolactam production without the need of the methylcyclopentanone removal distillation column 1084. At a minimum, the presence of the methylcyclopentylbenzene removal distillation column 1045 can reduce the size and energy consumption of the methylcyclopentanone removal column 1084, and/or improve the quality and quality consistency of the cyclohexanone product. Likewise, the phenol stream 1097 may comprise methylcyclopentylbenzene (especially MCPB2trans) at a very low concentration and may therefore be salable as a pure phenol product for use in bisphenol-A production without the need of the methylcyclopentylbenzene removal columns 1101 and 1107. At a minimum, the presence of the methylcyclopentylbenzene removal distillation column 1045 can reduce the size and energy consumption of the methylcyclopentylbenzene removal columns 1101 and 1107, and/or improve the quality and quality consistency of the phenol product.

As alternatives to the process and system illustrated in FIG. 1, one or more the following modifications are contemplated:

(a) One may choose not to include the methylcyclopentylbenzene removal column 1045, and therefore, include relatively large methylcyclopentanone removal columns 1084 and the phenol purification columns 1101 and 1107. This approach would result in the production of relatively large streams of methylcyclopentanone and methylcyclopentylbenzene (primarily MCPB2trans), which can be purified and used as valuable materials, such as specialty solvents.

(b) The recycle cyclohexylbenzene stream 1059 from the cyclohexylbenzene hydroperoxide concentrator 1057, upon optional purification, may bypass the methylcyclopentylbenzene removal column 1045 and be instead fed directly to the oxidation reactor 1051. This modification would result in a significantly reduced load to column 1045. However, it will increase the concentration of methylcyclopentylbenzene in the oxidation reactor, especially isomers of high boiling points such as MCPB1, MCPB2cis, and MCPB3s, which may be included in stream 1048 as discussed above, and hence higher concentration of methylcyclopentanone in stream 1085, therefore necessitate column 1084 at a relatively large size. Depending on whether conversion/isomerization between cyclohexylbenzene and/or the methylcyclopentylbenzene isomers takes place in the oxidation reactor 1051 and the cleavage reactor 1063, the phenol purification columns 1101 and 1107 for the purpose of methylcyclopentylbenzene removal may or may not be necessitated at different sizes.

(c) The recycle cyclohexylbenzene stream 1077 from the separation column 1073, upon optional purification and independent hydrogenation, may bypass the hydrogenation column 1042 and the methylcyclopentylbenzene removal column 1045, and be instead fed directly to the oxidation reactor 1051. Likewise, this modification would result in a significantly reduced load to column 1045. However, it will increase the concentration of methylcyclopentylbenzene in the oxidation reactor, especially isomers of high boiling points such as MCPB1, MCPB2cis, and MCPB3s, and hence higher concentration of methylcyclopentanone in stream 1085, therefore necessitate column 1084 at a relatively large size. Depending on whether conversion/isomerization between cyclohexylbenzene and/or the methylcyclopentylbenzene isomers takes place in the oxidation reactor 1051, the cleavage reactor 1063 and the hydrogenation step, the phenol purification columns 1101 and 1107 for the purpose of methylcyclopentylbenzene removal may or may not be necessitated at different sizes.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The contents of all references cited herein are incorporated by reference in their entirety.

The present invention includes one of more of the following non-limiting aspects and/or embodiments. It should be noted that, while the same symbol may be used to represent different variables in different paragraphs below, their respective meanings are independently defined in the same paragraph where they appear. For example, variables C1 and C2 are used the paragraphs describing both embodiments E4 and E5. However, their meanings are defined independently in the paragraphs where they appear.

E1. A process for making phenol and/or cyclohexanone, comprising:

(I) providing a first mixture comprising cyclohexylbenzene and methylcyclopentylbenzene;

(II) removing at least a portion of the methylcyclopentylbenzene from the first mixture to obtain a second mixture comprising cyclohexylbenzene;

(III) oxidizing at least a portion of the cyclohexylbenzene in the second mixture in an oxidation reactor under oxidation conditions to obtain a third mixture comprising cyclohexylbenzene hydroperoxide and cyclohexylbenzene; and (IV) reacting the cleavage feed in a cleavage reactor under cleavage reaction conditions to obtain a cleavage product mixture comprising cyclohexylbenzene, phenol and cyclohexanone.

E2. The process of E1, wherein the first mixture comprises methylcyclopentylbenzene at a concentration in a range from 100 ppm to 5.0 wt %, based on the total weight of the first mixture.

E3. The process of E1 or E2, wherein the first mixture comprises trans-1-methyl-2-phenylcyclopentane at a concentration in a range from 100 ppm to 4.5 wt %, based on the total weight of the first mixture.

E4. The process of any of the preceding embodiments, wherein the second mixture comprises methylcyclopentylbenzene at a concentration in a range from C1 ppm to C2 ppm, based on the total weight of the second mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 5000, as long as C1<C2.

E5. The process of any of the preceding embodiments, wherein the second mixture comprises trans-1-methyl-2-phenylcyclopentane at a concentration in a range from C1 ppm to C2 ppm, based on the total weight of the second mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E6. The process of any of the preceding embodiments, wherein the first mixture comprises methylcyclopentylbenzene at a concentration of C(MCPB)1, expressed as the weight percentage of methylcyclopentylbenzene based on the total weight of the first mixture, and the second mixture comprises methylcyclopentylbenzene at a concentration of C(MCPB)2, expressed as the weight percentage of methylcyclopentylbenzene based on the total weight of the second mixture, and R1≤C(MCPB)1/(MCPB)2≤R2, where R1 and R2 are, independently: 1.2, 1.4, 1.5, 1.6, 1.8, 2, 4, 5, 6, 8, 10, 20, 40, 50, 60, 80, 100, 200, 400, 600, 600, 800, 1000, as long as R1<R2.

E7. The process of any of the preceding embodiments, wherein the first mixture comprises MCPB2trans at a concentration of C(MCPB2trans)1, expressed as the weight percentage of MCPB2trans based on the total weight of the first mixture, and the second mixture comprises MCPB2trans at a concentration of C(MCPB2trans)2, expressed as the weight percentage of methylcyclopentylbenzene based on the total weight of the second mixture, and R1≤C(MCPBtrans2)1/C(MCPBtrans2)2≤R2, where R1 and R2 are, independently: 1.2, 1.4, 1.5, 1.6, 1.8, 2, 4, 5, 6, 8, 10, 20, 40, 50, 60, 80, 100, 200, 400, 600, 600, 800, 1000, as long as R1<R2.

E8. The process of any of the preceding embodiments, wherein the first mixture comprises MCPB2cis at a concentration of C(MCPB2cis)1, expressed as the weight percentage of MCPB2cis based on the total weight of the first mixture, and the second mixture comprises MCPB2cis at a concentration of C(MCPB2cis)2, expressed as the weight percentage of methylcyclopentylbenzene based on the total weight of the second mixture, and r1≤C(MCPB2cis)1/C(MCPB2cis)2≤r2, where r1 and r2 are, independently: 1.0, 1.1, 1.2, 1.3, 1.4, 1.5, 1.6, 1.7, 1.8, 1.9, 2.0, 3.0, 4.0, 5.0, 6.0, 7.0, 8.0, 9.0, 10, as long as r1<r2.

E9. The process of any of the preceding embodiments, wherein the third mixture comprises methylcyclopentylbenzene at a concentration in a range from C1 ppm to C2 ppm, based on the total weight of the second mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E10. The process of any of the preceding embodiments, wherein the third mixture comprises trans-1-methyl-2-phenylcyclopentane at a concentration in a range from C1 ppm to C2 ppm, based on the total weight of the second mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E11. The process of any of the preceding embodiments, wherein the cleavage product mixture comprises methylcyclopentylbenzene at a concentration in a range from C1 ppm to C2 ppm, based on the total weight of the cleavage product mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E12. The process of any of the preceding embodiments, wherein the cleavage product mixture comprises trans-1-methyl-2-phenylcyclopentane at a concentration in a range from C1 ppm to C2 ppm, based on the total weight of the cleavage product mixture, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E13. The process of any of the preceding embodiments, wherein the first mixture comprises cyclohexylbenzene at a concentration of at least C1 wt %, based on the total weight of the first mixture, where C1 can be: 90.0, 91.0, 92.0, 93.0, 94.0, 95.0, 96.0, 97.0, 98.0, 99.0, 99.1, 99.2, 99.3, 99.4, 99.5, 99.6, 99.7, 99.8, 99.9.

E14. The process of any of the preceding embodiments, wherein the second mixture comprises cyclohexylbenzene at a concentration of at least C1 wt %, based on the total weight of the first mixture, where C1 can be: 90.0, 91.0, 92.0, 93.0, 94.0, 95.0, 96.0, 97.0, 98.0, 99.0, 99.1, 99.2, 99.3, 99.4, 99.5, 99.6, 99.7, 99.8, 99.9.

E14a. The process of any of the preceding embodiments, wherein the first mixture comprises an olefin, and the process further comprises a step (Ic) between steps (I) and (II):

(Ic) subjecting the first mixture to hydrogenation in the presence of a hydrogenation catalyst comprising a hydrogenation metal.

E15. The process of any of the preceding embodiments, wherein step (I) comprises:

(Ia) contacting benzene with hydrogen in the presence of a hydroalkylation catalyst under hydroalkylation conditions to obtain a hydroalkylation product mixture; and (Ib) separating the hydroalkylation product mixture to obtain a fraction comprising cyclohexylbenzene and methylcyclopentylbenzene as the first mixture.

E16. The process of any of the preceding embodiments, wherein step (II) comprises distilling the first mixture.

E17. The process of any of the preceding embodiments, wherein step (III) comprises contacting a reaction medium in the oxidation reactor to oxygen in the presence of an oxidation catalyst represented by the following formula (FC-I), (FC-II) or (FC-III):

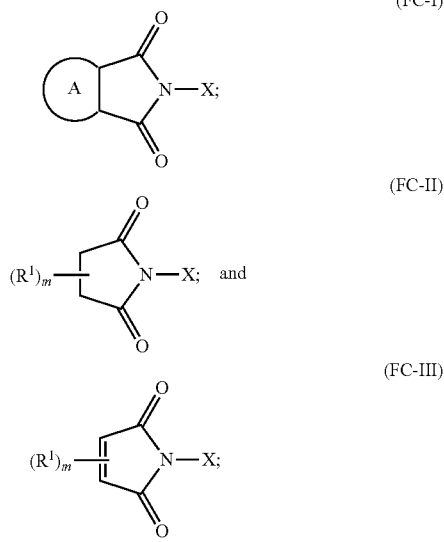

where:

A represents a ring optionally comprising nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1, or 2.

E18. The process of E17, wherein the oxidation catalyst is represented by the following formula (FC-IV):

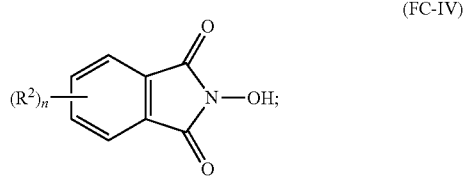

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

E19. The process of any of the preceding embodiments, wherein the third mixture comprises cyclohexylbenzene hydroperoxide at a concentration in a range from C1 wt % to C2 wt %, based on the total weight of the third mixture, where C1 and C2 can be, independently: 5.0, 6.0, 8.0, 10.0, 15.0, 20.0, 25.0, 30.0, 35.0, 40.0, 45.0, 50.0, 55.0, 60.0, as long as C1<C2.

E20. The process of any of the preceding embodiments, wherein step (IV) comprises:

(IV.1) separating at least a portion of the cyclohexylbenzene from the third mixture.

E21. The process of E20, wherein the cleavage teed comprises cyclohexylbenzene at a concentration in a range from C1 wt % to C2 wt %, based on the total weight of the cleavage feed, where C1 and C2 can be, independently: 10, 15, 20, 25, 30, 35, 40, 45, 50, 60, 65, 70, as long as C1<C2.

E22. The process of E21, wherein the cleavage feed comprises cyclohexylbenzene at a concentration in a range from C1 wt % to C2 wt %, based on the total weight of the cleavage feed, where C1 and C2 can be, independently: 20, 25, 30, 35, 40, 45, 50, 55, 60, as long as C1<C2.

E23. The process of any of the preceding embodiments, wherein the third mixture comprises cyclohexylbenzene at a concentration of C(CHBox), expressed in terms of weight percentage of cyclohexylbenzene based on the total weight of the third mixture, and the cleavage feed comprises cyclohexylbenzene at a concentration of C(CHBcf), expressed in terms of weight percentage of cyclohexylbenzene based on the total weight of the cleavage feed, wherein r1≤C(CHBox)/C(CHBcf)≤r2, where r1 and r2 can be, independently, 1.2, 1.4, 1.5, 1.6, 1.8, 2.0, 2.5, 3.0, 3.5, 4.0, 4.5, 5.0, as long as r1<r2.

E24. The process of any of the preceding embodiments, further comprising the following steps:

(IIIa) obtaining a fourth mixture comprising at least C1 wt % of cyclohexylbenzene, were C1 can be 80.0, 85.0, 90.0, 92.0, 94.0, 95.0, 96.0, 98.0, 99.0, 99.5, 99.8, 99.9, and a fifth mixture comprising cyclohexylbenzene hydroperoxide at a concentration higher than the third mixture; and (IIIb) feeding the fifth mixture to the cleavage reactor.

E25. The process of E24, wherein at least a portion of the fourth mixture is recycled to step (I) as at least a portion of the first mixture.

E26. The process of E25, wherein all of the first mixture is derived from the fourth mixture.

E27. The process of any of the preceding embodiments, further comprising:

(V) separating the cleavage product mixture to obtain a cyclohexylbenzene fraction, a phenol fraction and a cyclohexanone fraction.

E28. The process of E27, wherein the phenol fraction comprises methylcyclopentylbenzene at a concentration in a range from C1 ppm to C2 ppm, based on the total weight of the phenol fraction, where C1 and C2 can be, independently: 0.05, 0.08, 0.10, 0.20, 0.30, 0.40, 0.50, 0.60, 0.70, 0.80, 0.90, 1.0, 2.0, 4.0, 5.0, 6.0, 8.0, 10, 20, 40, 50, 60, 80, 100, 200, 400, 500, 600, 800, 1000, as long as C1<C2, and the process further comprises:

(VI) removing at least a portion of the methylcyclopentylbenzene from the phenol fraction.

E29. The process of E28, wherein the phenol fraction comprises trans-1-methyl-2-phenylcyclopentane at a concentration in a range from C1 ppm to C2 ppm, based on the total weight of the phenol fraction, where C1 and C2 can be, independently: 0.05, 0.08, 0.10, 0.20, 0.30, 0.40, 0.50, 0.60, 0.70, 0.80, 0.90, 1.0, 2.0, 4.0, 5.0, 6.0, 8.0, 10, 20, 40, 50, 60, 80, 100, 200, 400, 500, 600, 800, 1000, as long as C1<C2.

E30. The process of E28, wherein in step (VI) a purified phenol product comprising methylcyclopentylbenzene at a concentration below C1 ppm, based on the total weight of the purified phenol product, is obtained, where C1 can be: 1.0, 0.9, 0.8, 0.7, 0.6, 0.5, 0.4, 0.3, 0.2, 0.1.

E31. The process of E30, wherein the purified phenol product comprises trans-1-methyl-2-phenylcyclopentane at a concentration lower than C1 ppm, based on the total weight of the purified phenol product, where C1 can be: 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01.

E32. The process of any of the preceding embodiments E28 to E31, wherein step (VI) comprises:

(VIa) distilling the phenol fraction in the presence of an extractive solvent to obtain a fraction comprising methylcyclopentylbenzene and essentially free of the extractive solvent, and a fraction comprising a mixture of phenol and the extractive solvent; and (VIb) distilling the second fraction to obtain a fraction of purified phenol essentially free of methylcyclopentylbenzene.

E33. The process of E32, wherein the fraction of purified phenol comprises methylcyclopentylbenzene at a concentration lower than C1 ppm, based on the total weight of the purified phenol product, where C1 can be: 1.0, 0.9, 0.8, 0.7, 0.6, 0.5, 0.4, 0.3, 0.2, 0.1.

E34. The process of E33, wherein the fraction of purified phenol comprises trans-1-methyl-2-phenylcyclopentane at a concentration lower than C1 ppm, based on the total weight of the purified phenol product, where C1 can be: 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01.

E35. The process of any of E32 to E34, wherein the extractive solvent comprises a glycol.

E36. The process of E35, wherein the extractive solvent comprises diethylene glycol.

E37. The process of any of E27 to E36, wherein the cyclohexanone fraction comprises methylcyclopentanone at a concentration in a range from 50 ppb to 5.0 wt %, based on the total weight of the cyclohexanone fraction, and the process further comprises:

(VII) removing at least a portion of the methylcyclopentanone from the cyclohexanone fraction to obtain a purified cyclohexanone product.

E38. The process of E37, wherein the purified cyclohexanone product comprises methylcyclopentanone at a concentration below C1 ppm, based on the total weight of the purified cyclohexanone product, where C1 can be 50, 40, 30, 20, 10, 8, 6, 5, 4, 3, 2, 1.

E39. A process for making phenol and/or cyclohexanone, comprising:

(A) contacting benzene with hydrogen in the presence of a hydroalkylation catalyst under hydroalkylation conditions to obtain a hydroalkylation product mixture comprising cyclohexylbenzene;

(B) oxidizing at least a portion of the cyclohexylbenzene in an oxidation reactor under oxidation conditions to obtain an oxidation product mixture comprising cyclohexylbenzene hydroperoxide and cyclohexylbenzene;

(C) cleaving at least a portion of the cyclohexylbenzene hydroperoxide in a cleavage reactor under cleavage conditions to obtain a cleavage product mixture comprising cyclohexylbenzene, phenol, and cyclohexanone;

(D) separating the cleavage product mixture to obtain a cyclohexylbenzene fraction, a phenol fraction comprising methylcyclopentylbenzene, and a cyclohexanone fraction; and (E) removing at least a portion of the methylcyclopentylbenzene from the phenol fraction.

E40. The process of E39, wherein step (E) comprises:

(E1) distilling the phenol fraction in the presence of an extractive solvent to obtain a fraction comprising methylcyclopentylbenzene and essentially free of the extractive solvent, and a fraction comprising a mixture of phenol and the extractive solvent; and (E2) distilling the second fraction to obtain a fraction of purified phenol essentially free of methylcyclopentylbenzene.

E41. The process of E40, wherein the fraction of purified phenol comprises methylcyclopentylbenzene at a concentration lower than C1 ppm, based on the total weight of the purified phenol product, where C1 can be: 1.0, 0.9, 0.8, 0.7, 0.6, 0.5, 0.4, 0.3, 0.2, 0.1.

E42. The process of E41, wherein the fraction of purified phenol comprises trans-1-methyl-2-phenylcyclopentane at a concentration lower than C1 ppm, based on the total weight of the purified phenol product, where C1 can be: 1.0, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01.

E43. The process of E41 or E42, wherein the extractive solvent comprises a glycol.

E44. The process of E43, wherein the extractive solvent comprises diethyleneglycol.

E45. The process of any of the preceding embodiments E39 to E44, wherein the cyclohexanone fraction comprises methylcyclopentanone, and the process further comprises:

(F) removing at least a portion of the methylcyclopentanone from the cyclohexanone fraction to obtain a purified cyclohexanone product.

E46. The process of any of the preceding embodiments E39 to E45, further comprising:

(G) feeding at least a portion of the cyclohexylbenzene in the cyclohexylbenzene fraction obtained in step (D) to the oxidation reactor in step (B).

E47. The process of any of the preceding embodiments E39 to E46, further comprising:

(H) subjecting the cyclohexylbenzene fraction obtained in step (D) to hydrogenation.

E48. The process of E46 or E47, wherein the cyclohexylbenzene in the cyclohexylbenzene fraction obtained in step (D) comprises methylcyclopentylbenzene, and step (G) comprises:

(G1) removing at least a portion of the methylcyclopentylbenzene from the cyclohexylbenzene fraction obtained in step (D) to obtain a purified cyclohexylbenzene fraction; and (G2) feeding at least a portion of the purified cyclohexylbenzene fraction to the oxidation reactor in step (B).

E49. The process of any of the preceding embodiments E39 to E48, further comprising:

(B1) obtaining a recycle cyclohexylbenzene fraction essentially free of cyclohexylbenzene hydroperoxide (comprising cyclohexylbenzene hydroperoxide at a concentration no higher than C1 ppm, where C1 can be: 5000, 4000, 3000, 2000, 1000, 900, 800, 700, 600, 500, 400, 300, 200, 100, 90, 80, 70, 60, 50, 40, 30, 20, 10, 9, 6, 5, 4, 3, 2, or 1) and a cyclohexylbenzene hydroperoxide fraction from the oxidation product mixture;

(B2) feeding at least a portion of the cyclohexylbenzene in the recycle cyclohexylbenzene fraction to the oxidation reactor in step (B); and (B3) feeding at least a portion of the cyclohexylbenzene hydroperoxide in the cyclohexylbenzene hydroperoxide fraction to the cleavage reactor in step (C).

E50. The process of E49, wherein the recycle cyclohexylbenzene fraction comprises methylcyclopentylbenzene, and step (B2) comprises:

(B2a) removing at least a portion of the methylcyclopentylbenzene from the recycle cyclohexylbenzene fraction to obtain a purified recycle cyclohexylbenzene fraction; and (B2b) feeding at least a portion of the purified recycle cyclohexylbenzene fraction to the oxidation reactor in step (B).

E51. The process of any of the preceding embodiments E39 to E50, wherein the hydroalkylation product mixture comprises methylcyclopentylbenzene at a concentration in a range from 100 ppm to 5.0 wt %, based on the total weight of the hydroalkylation product mixture.

E52. The process of any of the preceding embodiments E39 to E51, wherein the hydroalkylation product mixture further comprises methylcyclopentylbenzene, and the process further comprises:

(A1) separating the hydroalkylation product mixture to obtain a purified cyclohexylbenzene fraction; and (A2) feeding at least a portion of the cyclohexylbenzene in the purified cyclohexylbenzene fraction to the oxidation reactor in step (B).

E53. The process of E52, wherein the purified cyclohexylbenzene fraction obtained in step (A2) comprises methylcyclopentylbenzene at a concentration in a range from C1 ppm to C2 ppm, based on the total weight of the purified cyclohexylbenzene fraction, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 5000, as long as C1<C2.

E54. The process of E52 or E53, wherein the purified cyclohexylbenzene fraction obtained in step (A2) comprises cis-1-methyl-2-phenylcyclopentane at a concentration in a range from C1 ppm to C2 ppm, based on the total weight of the purified cyclohexylbenzene fraction, where C1 and C2 can be, independently: 0, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 5000, as long as C1<C2.

E55. A phenol composition comprising phenol at a concentration of C(Phenol) wt % and methylcyclopentylbenzene at a concentration of C(MCPB) ppm, where:

the percentage and ppm are based on the total weight of the phenol composition;

C(Phenol)≥C1;

C1 can be 95.00, 96.00, 97.00, 98.00, 99.00, 99.20, 99.40, 99.50, 99.80, 99.90, 99.92, 99.94, 99.95, 99.96, 99.98, 99.99;

C2≤C(MCPB)≤C3; and

C2 and C3 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, as long as C2<C3.

E56. The phenol composition of E55, wherein 0.010≤C(MCPB)≤20.

E57. The phenol composition of E55 or E56, wherein the methylcyclopentylbenzene comprises (a) cis-1-methyl-2-phenylcyclopentane at a concentration of C(MCPB2cis) ppm and (b) trans-1-methyl-2-phenylcyclopentane at a concentration of C(MCPB2trans) ppm, and at least one of the following conditions (i), (ii), and (iii) is met:

(i) C1≤C(MCPB2cis)≤C2, where C1 and C2 can be, independently, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 45, as long C1<C2;

(ii) C3≤C(MCPB2trans)≤C4, where C3 and C4 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long as C3<C4; and (iii) C5≤C(MCPB2cis)+C(MCPB2trans)≤C6, where C5 and C6 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long as C5<C6.

E58. The phenol composition of any of the preceding embodiments E55 to E57, wherein the methylcyclopentylbenzene comprises (a) cis-1-methyl-2-phenylcyclopentane at a concentration of C(MCPB2cis) ppm and (b) trans-1-methyl-2-phenylcyclopentane at a concentration of C(MCPB2trans) ppm, and C(MCPB2trans)>C(MCPB2cis).

E59. The phenol composition of any of the preceding embodiments E55 to E58, wherein r1≤C(MCPB2trans)/C(MCPB2cis)≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2.

E60. The phenol composition of any of the preceding embodiments E55 to E59, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; (c) cis-1-methyl-3-phenylcyclopentane at a concentration of C(MCPB3cis) ppm; and (d) trans-1-methyl-3-phenylcyclopentane at a concentration of C(MCPB3trans) ppm, and at least one of the following conditions (i), (ii), and (iii) is met:

(i) C(MCPB2cis)+C(MCPB2trans)>C(MCPB3cis)+C(MCPB3trans);

(ii) r1≤C(MCPB2trans)/(C(MCPB3cis)+C(MCPB3trans))≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2; and (iii) r3≤(C(MCPB2cis)+C(MCPB2trans))/(C(MCPB3cis)+C(MCPB3trans))≤r4, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4.

E61. The phenol composition of any of the preceding embodiments E55 to E60, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; (c) 1-methyl-1-phenylcyclopentane at a concentration of C(MCPB1) ppm; and at least one of the following conditions (i), (ii), (iii), and (iv) is met:

(i) C(MCPB2cis)+C(MCPB2trans)>C(MCPB1);

(ii) C(MCPB2trans)>C(MCPB1);

(iii) r1≤C(MCPB2trans)/C(MCPB1)≤r2, where r1 and r2 can be independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2; and (iv) r3≤C(MCPB2cis)+C(MCPB2trans))/(C(MCPB1)≤r4, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4.

E62. The phenol composition of the preceding embodiments E55 to E61, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; and (c) 1-methyl-1-phenylcyclopentane at a concentration of C(MCPB1) ppm; (d) cis-1-methyl-3-phenylcyclopentane at a concentration of C(MCPB3cis) ppm; and (e) trans-1-methyl-3-phenylcyclopentane at a concentration of C(MCPB3trans) ppm, and at least one of the following conditions (i), (ii), and (iii) is met:

(i) C(MCPB2cis)+C(MCPB2trans)>C(MCPB1)+C(MCPB3cis)+C(MCPB3trans);

(ii) r1≤C(MCPB2trans)/(C(MCPB1)+C(MCPB3cis)+C(MCPB3trans))≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2; and (iii) r3≤(C(MCPB2cis)+C(MCPB2trans))/(C(MCPB1)+C(MCPB3cis)+C(MCPB3trans))≤r4, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4.

E63. The phenol composition of any of the preceding embodiments E55 to E62, wherein the methylcyclopentylbenzene comprises cis-1-methyl-3-phenylcyclopentane at a concentration of C(MCPB3cis) ppm and trans-1-methyl-3-phenylcyclopentane at a concentration of C(MCPB3trans) ppm, and at least one of the following conditions (i), (ii), and (iii) is met:

(i) C1≤C(MCPB3cis)≤C2, where C1 and C2 can be, independently, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long C1<C2;

(ii) C3≤(MCPB3trans)≤C4, where C3 and C4 can be, independently, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long C3<C4; and (iii) C5≤C(MCPB3cis)+C(MCPB3trans)≤C6, where C5 and C6 can be, independently, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long C5<C6.

E64. The phenol composition of any of the preceding embodiments E55 to E63, wherein the methylcyclopentylbenzene comprises 1-methyl-1-phenylcyclopentane at a concentration of C(MCPB1) ppm, and C1≤C(MCPB1)≤C2, where C1 and C2 can be, independently, 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, as long C1<C1.

E65. A phenol composition comprising phenol at a concentration of C(Phenol) and trans-1-methyl-2-phenylcyclopentane at a concentration of C(MCPB2trans), wherein the ratio C(Phenol)/C(MCPB2trans) is equal to the ratio C(PhenolAz)/C(MCPB2transAz), where C(PhenolAz) and C(MCPB2transAz) are concentrations of phenol and MCPB2trans in a binary azeotrope between phenol and trans-1-methyl-2-phenylcyclopentane, respectively.

E66. A phenol composition consisting of a binary azeotrope between phenol and trans-1-methyl-2-phenylcyclopentane.

E67. A cyclohexylbenzene composition comprising cyclohexylbenzene at a concentration of C(CHB) wt % and methylcyclopentylbenzene at a concentration of C(MCPB) ppm, where the percentage and ppm are based on the total weight of the phenol composition;

C(CHB)≥C1;

C1 can be 95.00, 96.00, 97.00, 98.00, 99.00, 99.20, 99.40, 99.50, 99.80, 99.90, 99.92, 99.94, 99.95, 99.96, 99.98, 99.99;

C2≤C(MCPB)≤C3; and

C2 and C3 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, 5000, as long as C1<C2.

E68. The cyclohexylbenzene composition of E67, wherein 0.010≤C(MCPB)≤1000.

E69. The cyclohexylbenzene composition of E67 or E68, wherein the methylcyclopentylbenzene comprises (a) cis-1-methyl-2-phenylcyclopentane at a concentration of C(MCPB2cis) ppm and (b) trans-1-methyl-2-phenylcyclopentane at a concentration of C(MCPB2trans) ppm, and at least one of the following conditions (i), (ii), and (iii) is met:

(i) C1≤C(MCPB2cis)≤C2, where C1 and C2 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2;

(ii) C3≤C(MCPB2trans)≤C4, where C3 and C4 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C3<C4; and (iii) C5≤C(MCPB2cis)+C(MCPB2trans)≤C6, where C5 and C6 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C5<C6.

E70. The cyclohexylbenzene composition of any of the preceding embodiments E67 to E69, wherein the methylcyclopentylbenzene comprises (a) cis-1-methyl-2-phenylcyclopentane at a concentration of C(MCPB2cis) ppm and (b) trans-1-methyl-2-phenylcyclopentane at a concentration of C(MCPB2trans) ppm, and C(MCPB2trans)>C(MCPB2cis).

E71. The cyclohexylbenzene composition of the preceding embodiments E67 to E70, wherein 1.5≤C(MCPB2trans)/C(MCPB2cis)≤1000.

E72. The cyclohexylbenzene composition of any of the preceding; embodiments E67 to E71, wherein the methylcyclopentylbenzene comprises (a) cis-1-methyl-2-phenylcyclopentane at a concentration of C(MCPB2cis) ppm and (b) trans-1-methyl-2-phenylcyclopentane at a concentration of C(MCPB2trans) ppm, and C(MCPB2trans)<C(MCPB2cis).

E73. The cyclohexylbenzene composition of the preceding embodiments E67, E68, E69, and E72, wherein r1≤C(MCPB2cis)/C(MCPB2trans)≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2.

E74. The cyclohexylbenzene composition of any of the preceding embodiments E67 to E73, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; (c) cis-1-methyl-3-phenylcyclopentane at a concentration of C(MCPB3cis) ppm; and (d) trans-1-methyl-3-phenylcyclopentane at a concentration of C(MCPB3trans) ppm, and at least one of the following conditions (i), (ii (iii), and (iv) is met:
  (i) C(MCPB2cis)+C(MCPB2trans)>C(MCPB3cis)+C(MCPB3trans);
  (ii) r1≤C(MCPB2trans)/(C(MCPB3cis)+C(MCPB3trans))≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2;
  (iii) r3≤C(MCPB2cis)/(C(MCPB3cis)+C(MCPB3trans))≤r3, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4; and
  (iv) r5≤(C(MCPB2cis)+C(MCPB2trans))/(C(MCPB3cis)+C(MCPB3trans))≤r6, where r5 and r6 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r5<r6.

E75. The cyclohexylbenzene composition of any of the preceding embodiments E67 to E74, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; and (c) 1-methyl-1-phenylcyclopentane at a concentration of C(MCPB1) ppm; and at least one of the following conditions (i), (ii), (iii), and (iv) is met:
  (i) C(MCPB2cis)+C(MCPB2trans)>C(MCPB1);
  (ii) C(MCPB2trans)>C(MCPB1);
  (iii) r1≤C(MCPB2trans)/C(MCPB1)≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2; and
  (iv) r3≤(C(MCPB2cis)+C(MCPB2trans))/(C(MCPB1)≤r4, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4.

E76. The cyclohexylbenzene composition of the preceding embodiments E67 to E75, wherein the methylcyclopentylbenzene comprises (a) cis-1-methyl-2-phenylcyclopentane at a concentration of C(MCPB2cis) ppm; (b) trans-1-methyl-2-phenylcyclopentane at a concentration of C(MCPB2trans) ppm; and (c) 1-methyl-1-phenylcyclopentane at a concentration of C(MCPB1) ppm; (d) cis-1-methyl-3-phenylcyclopentane at a concentration of C(MCPB3cis) ppm; and (e) trans-1-methyl-3-phenylcyclopentane at a concentration of C(MCPB3trans) ppm, and at least one of the following conditions (i) and (ii) is met:
  (i) C(MCPB2cis)+C(MCPB2trans)>C(MCPB1)+C(MCPB3cis)+C(MCPB3trans);
  (ii) r1≤C(MCPB2trans)/(C(MCPB1)+C(MCPB3cis)+C(MCPB3trans))≤r2, where r1 and r2 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r1<r2; and
  (iii) r3≤(C(MCPB2cis)+C(MCPB2trans))/(C(MCPB)+C(MCPB3cis)+C(MCPB3trans))≤r4, where r3 and r4 can be, independently: 1.2, 1.4, 1.5, 1.6, 1.8, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, as long as r3<r4.

E77. The cyclohexylbenzene composition of any of the preceding embodiments E67 to E76, wherein the methylcyclopentylbenzene comprises cis-1-methyl-3-phenylcyclopentane at a concentration of C(MCPB3cis) ppm and trans-1-methyl-3-phenylcyclopentane a concentration of C(MCPB3trans) ppm, and at least one of the following conditions (i), (ii), and (iii) is met:
  (i) C1≤C(MCPB3cis)≤C2, where C1 and C2 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2;
  (ii) C3≤(MCPB3trans)≤C4, where C3 and C4 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C3<C4; and
  (iii) C5≤C(MCPB3cis)+C(MCPB3trans)≤C6, where C5 and C6 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C5<C6.

E78. The cyclohexylbenzene composition of any of the preceding embodiments E67 to E77, wherein the methylcyclopentylbenzene comprises 1-methyl-1-phenylcyclopentane at a concentration of C(MCPB1) ppm, and C1≤C(MCPB1)≤C2, where C1 and C2 can be, independently: 0.001, 0.002, 0.003, 0.004, 0.005, 0.006, 0.007, 0.008, 0.009, 0.010, 0.020, 0.030, 0.040, 0.050, 0.060, 0.070, 0.080, 0.090, 0.10, 0.20, 0.30, 0.40, 0.50, 0.60, 0.70, 0.80, 0.90, 1.0, 2.0, 3.0, 4.0, 5.0, 6.0, 7.0, 8.0, 9.0, 10, 20, 30, 40, 50, 60, 70, 80, 90, 100, 200, 300, 400, 500, 600, 700, 800, 900, 1000, 2000, 3000, 4000, 4500, as long as C1<C2.

E79. The cyclohexylbenzene composition of any of the preceding embodiments E67 to E78, further comprising phenol at a concentration no greater than C1 ppm, expressed as the weight percentage of phenol on the basis of the total weight of the cyclohexylbenzene composition, where C1 can be: 50, 40, 30, 20, 10, 8, 6, 5, 4, 2, 1.

E80. The cyclohexylbenzene composition of any of the preceding embodiments E67 to E79, further comprising cyclohexenylbenzene at a concentration no greater than C1 ppm, expressed as the weight percentage of cyclohexenylbenzene on the basis of the total weight of the cyclohexylbenzene composition, where C1 can be: 50, 40, 30, 20, 10, 8, 6, 5, 4, 2, 1.

The invention claimed is:

1. A process for making phenol and/or cyclohexanone, the process comprising:
   (I) providing a first mixture comprising cyclohexylbenzene and methylcyclopentylbenzene, wherein the first mixture comprises methylcyclopentylbenzene at a concentration in a range from 100 ppm to 5.0 wt %, based on the total weight of the first mixture, and wherein the first mixture comprises trans-1-methyl-2-phenylcyclopentane at a concentration in a range from 100 ppm to 4.5 wt %, based on the total weight of the first mixture;
   (II) removing at least a portion of the methylcyclopentylbenzene from the first mixture to obtain a second mixture comprising cyclohexylbenzene, wherein the second mixture comprises methylcyclopentylbenzene at a concentration in a range from 0 ppm to 2000 ppm, based on the total weight of the second mixture;
   (III) oxidizing at least a portion of the cyclohexylbenzene in the second mixture in an oxidation reactor under oxidation conditions to obtain a third mixture comprising cyclohexylbenzene hydroperoxide and cyclohexylbenzene; and
   (IV) reacting at least a portion of the third mixture in a cleavage reactor under cleavage reaction conditions to obtain a cleavage product mixture comprising cyclohexylbenzene, phenol and cyclohexanone.

2. The process of claim 1, wherein the cleavage product mixture comprises trans-1-methyl-2-phenylcyclopentane at a concentration in a range from 100 ppb to 2000 ppm, based on the total weight of the cleavage product mixture.

3. The process of claim 1, wherein step (I) comprises:
   (Ia) contacting benzene with hydrogen in the presence of a hydroalkylation catalyst under hydroalkylation conditions to obtain a hydroalkylation product mixture; and
   (Ib) separating the hydroalkylation product mixture to obtain a fraction comprising cyclohexylbenzene and methylcyclopentylbenzene as the first mixture.

4. The process of claim 1, further comprising the following steps:
   (IIIa) obtaining a fourth mixture comprising at least 80 wt % of cyclohexylbenzene and a fifth mixture comprising cyclohexylbenzene hydroperoxide at a concentration higher than the third mixture; and
   (IIIb) feeding the fifth mixture to the cleavage reactor as a portion of the third mixture.

5. The process of claim 4, wherein at least a portion of the fourth mixture is recycled to step (I) as at least a portion of the first mixture.

6. The process of claim 1, further comprising:
   (V) separating the cleavage product mixture to obtain a cyclohexylbenzene fraction, a phenol fraction and a cyclohexanone fraction.

7. The process of claim 6, wherein the phenol fraction comprises methylcyclopentylbenzene at a concentration in a range from 50 ppb to 1000 ppm, based on the total weight of the phenol fraction, and the process further comprises:
   (VI) removing at least a portion of the methylcyclopentylbenzene from the phenol fraction.

8. The process of claim 7, wherein the phenol fraction comprises trans-1-methyl-2-phenylcyclopentane at a concentration in a range from 50 ppb to 750 ppm, based on the total weight of the phenol fraction.

9. The process of claim 7, wherein in step (VI), a purified phenol product comprising methylcyclopentylbenzene at a concentration below 1 ppm, based on the total weight of the purified phenol product, is obtained, further wherein the purified phenol product comprises trans-1-methyl-2-phenylcyclopentane at a concentration lower than 950 ppb, based on the total weight of the purified phenol product.

10. The process of claim 7, wherein step (VI) comprises:
    (VIa) distilling the phenol fraction in the presence of an extractive solvent to obtain a fraction comprising phenol and essentially free of the extractive solvent, and a fraction comprising a mixture of methylcyclopentylbenzene and the extractive solvent.

* * * * *